US012805868B2

(12) United States Patent
Holdmeyer et al.

(10) Patent No.: US 12,805,868 B2
(45) Date of Patent: Nov. 24, 2026

(54) ELECTRONICS INFRASTRUCTURE OF AN END EFFECTOR FOR SURGICAL STAPLING INSTRUMENTS

(71) Applicant: Cilag GmbH International, Zug (CH)

(72) Inventors: Seth Holdmeyer, Cincinnati, OH (US); Adam Hensel, Gahanna, OH (US); Thomas Brent Remm, Milford, OH (US)

(73) Assignee: Cilag GmbH International, Zug (CH)

(*) Notice: Subject to any disclaimer, the term of this patent is extended or adjusted under 35 U.S.C. 154(b) by 0 days.

(21) Appl. No.: 19/212,556

(22) Filed: May 19, 2025

(65) Prior Publication Data

US 2026/0363700 A1 Nov. 19, 2026

(51) Int. Cl.

| | |
|---|---|
| ***A61B 17/072*** | (2006.01) |
| ***A61B 17/00*** | (2006.01) |
| *A61B 34/30* | (2016.01) |

(52) U.S. Cl.

CPC .................. *A61B 17/07207* (2013.01); *A61B 2017/00039* (2013.01); *A61B 2017/00221* (2013.01); *A61B 2017/00398* (2013.01); *A61B 2017/00477* (2013.01); *A61B 2017/07257* (2013.01); *A61B 2017/07285* (2013.01); *A61B 34/30* (2016.02)

(58) Field of Classification Search

CPC ................................................ A61B 17/07207

See application file for complete search history.

(56) References Cited

U.S. PATENT DOCUMENTS

| | | | |
|---|---|---|---|
| 5,395,033 A | 3/1995 | Byrne et al. | |
| 7,644,848 B2 | 1/2010 | Swayze et al. | |
| 7,721,931 B2 | 5/2010 | Shelton, IV et al. | |
| 8,753,338 B2 | 6/2014 | Widenhouse et al. | |
| 9,265,585 B2 | 2/2016 | Wingardner et al. | |
| 9,615,888 B2 | 4/2017 | Manzo et al. | |
| 9,668,735 B2 | 6/2017 | Beetel | |
| 9,877,718 B2 | 1/2018 | Weir et al. | |
| 10,190,888 B2 | 1/2019 | Hryb et al. | |
| 10,206,678 B2 | 2/2019 | Shelton, IV et al. | |
| 10,271,844 B2 | 4/2019 | Valentine et al. | |
| 10,595,836 B2 | 3/2020 | Smaby et al. | |
| 10,603,117 B2 * | 3/2020 | Schings | A61B 17/295 |

(Continued)

FOREIGN PATENT DOCUMENTS

| | | | |
|---|---|---|---|
| EP | 0679367 | A2 | 11/1995 |
| EP | 2364666 | A1 | 9/2011 |
| WO | 2012112249 | A1 | 8/2012 |

*Primary Examiner* — Joshua G Kotis

(74) *Attorney, Agent, or Firm* — Barnes & Thornburg LLP

(57) ABSTRACT

A surgical instrument includes an end effector having an elongated jaw with a pair of side walls separated by a floor, which define a cavity positioned at a proximal end of the jaw and a channel extending from the cavity to a distal end. The surgical instrument includes an I-beam having a knife and moveable from a position within the cavity to another position at the distal end of the channel. A circuit board is coupled to the jaw within the cavity, adjacent to the I-beam when the I-beam is within the cavity. A side wall may include an inner surface defining an inner groove within the channel, and another circuit board may be coupled to the side wall within the inner groove. A board support that supports the circuit board may be positioned in the cavity. Other embodiments are described and claimed.

7 Claims, 20 Drawing Sheets

(56) References Cited

U.S. PATENT DOCUMENTS

| | | | | |
|---|---|---|---|---|
| 10,639,038 | B2 * | 5/2020 | Scott | A61B 17/07292 |
| 10,828,030 | B2 | 11/2020 | Weir et al. | |
| 11,559,366 | B2 | 1/2023 | Overmyer et al. | |
| 11,653,915 | B2 | 5/2023 | Shelton, IV et al. | |
| 11,937,816 | B2 | 3/2024 | Huang | |
| 11,992,210 | B2 | 5/2024 | Shelton, IV et al. | |
| 12,082,806 | B2 | 9/2024 | Giordano et al. | |
| 12,171,428 | B2 * | 12/2024 | Shelton, IV | A61B 17/072 |
| 12,193,670 | B1 * | 1/2025 | Shelton, IV | A61B 17/07207 |
| 12,268,388 | B2 | 4/2025 | Fiebig et al. | |
| 12,484,900 | B2 | 12/2025 | Ryle et al. | |
| 12,544,067 | B2 | 2/2026 | Batty et al. | |
| 2015/0196348 | A1 * | 7/2015 | Yates | A61B 90/98<br>227/182.1 |
| 2016/0030042 | A1 | 2/2016 | Heinrich et al. | |
| 2017/0296189 | A1 * | 10/2017 | Vendely | A61B 17/07207 |
| 2018/0042658 | A1 | 2/2018 | Shelton, IV et al. | |
| 2019/0000538 | A1 * | 1/2019 | Widenhouse | A61B 17/07207 |
| 2019/0015102 | A1 | 1/2019 | Baber et al. | |
| 2019/0200997 | A1 | 7/2019 | Shelton, IV et al. | |
| 2019/0290270 | A1 * | 9/2019 | Bakos | A61B 17/072 |
| 2020/0405301 | A1 * | 12/2020 | Shelton, IV | A61B 17/1155 |
| 2021/0100579 | A1 * | 4/2021 | Shelton, IV | A61B 17/320092 |
| 2022/0273305 | A1 * | 9/2022 | Shelton, IV | G16H 40/63 |
| 2023/0049736 | A1 * | 2/2023 | Shelton, IV | A61B 90/30 |
| 2023/0051361 | A1 * | 2/2023 | Shelton, IV | A61B 34/00 |
| 2023/0346372 | A1 * | 11/2023 | Shelton, IV | A61B 17/0686 |
| 2024/0032920 | A1 * | 2/2024 | Shelton, IV | A61B 17/07207 |
| 2024/0366221 | A1 | 11/2024 | Marriott et al. | |
| 2024/0415510 | A1 | 12/2024 | Schings et al. | |
| 2024/0423615 | A1 | 12/2024 | Shelton, IV et al. | |
| 2025/0000510 | A1 | 1/2025 | Creamer et al. | |
| 2025/0017585 | A1 | 1/2025 | Nalagatla et al. | |
| 2025/0025155 | A1 | 1/2025 | Batty et al. | |
| 2025/0025156 | A1 | 1/2025 | Shelton, IV et al. | |
| 2025/0025157 | A1 | 1/2025 | Batty et al. | |
| 2025/0025158 | A1 | 1/2025 | Ryle et al. | |
| 2025/0025159 | A1 | 1/2025 | Batty et al. | |
| 2025/0025160 | A1 | 1/2025 | Batty et al. | |
| 2025/0025162 | A1 | 1/2025 | Ahrens et al. | |
| 2025/0025164 | A1 | 1/2025 | Batty et al. | |
| 2025/0025165 | A1 | 1/2025 | Ryle et al. | |
| 2025/0025167 | A1 | 1/2025 | Ryle et al. | |
| 2025/0025168 | A1 | 1/2025 | Ryle et al. | |
| 2025/0025169 | A1 | 1/2025 | Batty et al. | |
| 2025/0025170 | A1 | 1/2025 | Bertram et al. | |
| 2025/0120718 | A1 | 4/2025 | Shelton, IV et al. | |
| 2025/0312040 | A1 | 10/2025 | Overmyer | |
| 2025/0375200 | A1 | 12/2025 | Batty et al. | |

* cited by examiner

ELECTRONICS INFRASTRUCTURE OF AN END EFFECTOR FOR SURGICAL STAPLING INSTRUMENTS

TECHNICAL FIELD

The present disclosure relates generally to surgical instruments and, more particularly, to surgical stapling and cutting instruments and associated staple cartridges for use with the surgical instruments to facilitate the cutting and stapling of patient tissue.

BACKGROUND

Surgical procedures often involve the use of various surgical instruments to assist a surgeon in the performance of the corresponding procedure. Recently, minimally invasive surgical (MIS) instruments have gained preference over traditional "open" surgical devices as the use of MIS instruments can reduce post-operative recovery time and associated tissue scarring. Endoscopy and laparoscopy are common types of MIS procedures in which a tube or trocar is inserted into natural or surgically-made openings (e.g., incisions) of the patient, depending on the particular procedure. The tube or trocar is then used to facilitate introduction of associated surgical instruments into the patient's body (e.g., the patient's abdominal cavity) to treat internal tissue of the patient.

One type of surgical instrument usable in MIS procedures is a surgical stapler, sometimes referred to as an "endocutter." A typical surgical stapler includes an elongated shaft to facilitate use of a trocar and an end effector located at a distal end of the elongated shaft. The elongated shaft facilitates the use of the surgical stapler with a trocar to access the patient's anatomical environment (e.g., the patient's abdominal cavity) and may include one or more articulation joints to increase the usability of the surgical stapler in the anatomical environment. Similarly, the end effector may be attached to the elongated shaft via an articulation joint to allow the end effector to be positioned as desired by the surgeon. A typical end effector of a surgical stapler includes a pair of jaws movable between an open position and a closed position to facilitate the grasping of tissue within the jaws. One of the jaws is embodied as a cartridge jaw and is configured to receive a staple cartridge, and the other jaw is embodied as an anvil jaw configured to provide a surface on which the staples are formed. The end effector also includes a cutting element (typically referred to as a "knife"), which is translated distally along the end effector during a firing phase of the surgical stapler to transect tissue presently grasped by the end effector. As the knife advances along the end effector, staples contained in the staple cartridge are progressively ejected to thereby seal opposing sides of the transected tissue.

Surgical staplers may be embodied as independent, hand-held devices or configured to be coupled to a robotic surgery system. In hand-held embodiments, the surgical stapler may include a handle and an associated trigger, which is operable by a surgeon to control the end effector and the ejection of the staples from the staple cartridge. In robotic embodiments, the surgical stapler is configured to be mounted to a robotic arm of a robotic manipulator, which is controllable by the surgeon via a remote control console. For example, the control console may include various input devices that can be grasped and manipulated by the surgeon to cause movement and firing of the surgical stapler.

SUMMARY

According to one aspect, a surgical instrument includes an end effector, an I-beam including a knife, and a first circuit board. The end effector includes an elongated jaw that extends from a proximal end to a distal end. The jaw includes a first side wall, a second side wall, and a floor coupled between the first side wall and the second side wall. The first side wall, the second side wall, and the floor cooperate to define a first cavity positioned at the proximal end and a channel extending from the first cavity to the distal end. The I-beam is moveable from a first position within the first cavity to a second position at the distal end of the channel. The first circuit board is coupled to the elongated jaw within the first cavity. The first circuit board is adjacent to the I-beam when the I-beam is in the first position.

In an embodiment, the first circuit board is coupled to the first side wall. In an embodiment, the surgical instrument further includes a second circuit board coupled to the floor of the elongated jaw within the first cavity and a first flex connector that electrically couples the first circuit board and the second circuit board. In an embodiment, the floor of the elongated jaw defines an elongated slot that extends from the first cavity to the distal end. The second circuit board includes a first section and a second section that cooperate to define a gap between the first section and the second section. The gap is aligned with the elongated slot. In an embodiment, the surgical instrument further includes third circuit board coupled to the second side wall within the first cavity, and a second flex connector that electrically couples the second circuit board and the third circuit board.

In an embodiment, the first side wall includes an inner wall surface that faces the channel. The first side wall defines a first inner groove that is in communication with the channel. The surgical instrument further includes a second circuit board coupled to the first side wall within the first inner groove and a first flex connector that electrically couples the first circuit board and the second circuit board.

In an embodiment, the first side wall includes an outer wall surface. The outer wall surface defines a first outer groove. A first opening is defined in the first side wall. The first opening is in communication with the channel. The surgical instrument further includes a second circuit board coupled to the first side wall within the first outer groove. The second circuit board is electrically coupled to the first circuit board via the first opening.

In an embodiment, the first circuit board includes a processing circuit or a sensing circuit.

In an embodiment, the surgical instrument further includes a board support coupled to the elongated jaw and positioned within the first cavity. The board support includes a first arm and a second arm coupled by a bend. The first arm and the second arm define an opening toward the distal end of the elongated jaw. The first arm and the second arm surround the I-beam when the I-beam is in the first position. The first arm supports the first circuit board. The first circuit board is adjacent to and aligned with the first side wall. In an embodiment, the surgical instrument further includes a permanent magnet coupled to the second arm of the board support. The permanent magnet is positioned opposite the first circuit board across the opening defined between the first arm and the second arm. In an embodiment, the surgical instrument further includes a magnetic sensor coupled to the first circuit board and positioned opposite the permanent magnet. In an embodiment, the surgical instrument further includes a near-field communication antenna board electrically coupled to the first circuit board and extending toward the distal end of the elongated jaw. The near-field communication antenna board is adjacent to and aligned with the first side wall.

In an embodiment, the surgical instrument further includes an elongated shaft that extends from a distal end to a proximal end. The distal end is coupled to the end effector. The elongated shaft includes a drivetrain coupled to the I-beam and a flexible connector electrically coupled to the first circuit board and extending through the elongated shaft. In an embodiment, the surgical instrument further includes a handpiece or a robotic tool interface coupled to the proximal end of the elongated shaft. The handpiece or the robotic tool interface is electrically coupled to the flexible connector and is configured to drive the drivetrain. In an embodiment, the elongated shaft includes a joint, the flexible connector includes a slack bend positioned at the joint, and the joint includes a boss extending from the shaft that retains the flexible connector within a boundary of the elongated shaft.

In an embodiment, the surgical instrument further includes an elongated anvil extending from a proximal end to a distal end. The proximal end is hingedly coupled to a hinge positioned at the proximal end of the elongated jaw. The anvil is rotatable about the hinge from an open position in which the distal end of the anvil is spaced apart from the distal end of the jaw, to a closed position in which the distal end of the anvil is close to the distal end of the jaw. In an embodiment, the surgical instrument further includes a leaf spring positioned in the first cavity and configured to bias the anvil to the open position. The leaf spring is positioned between the board support and the anvil.

BRIEF DESCRIPTION OF THE DRAWINGS

The detailed description particularly refers to the following figures, in which.

DETAILED DESCRIPTION OF THE DRAWINGS

Figure 1:
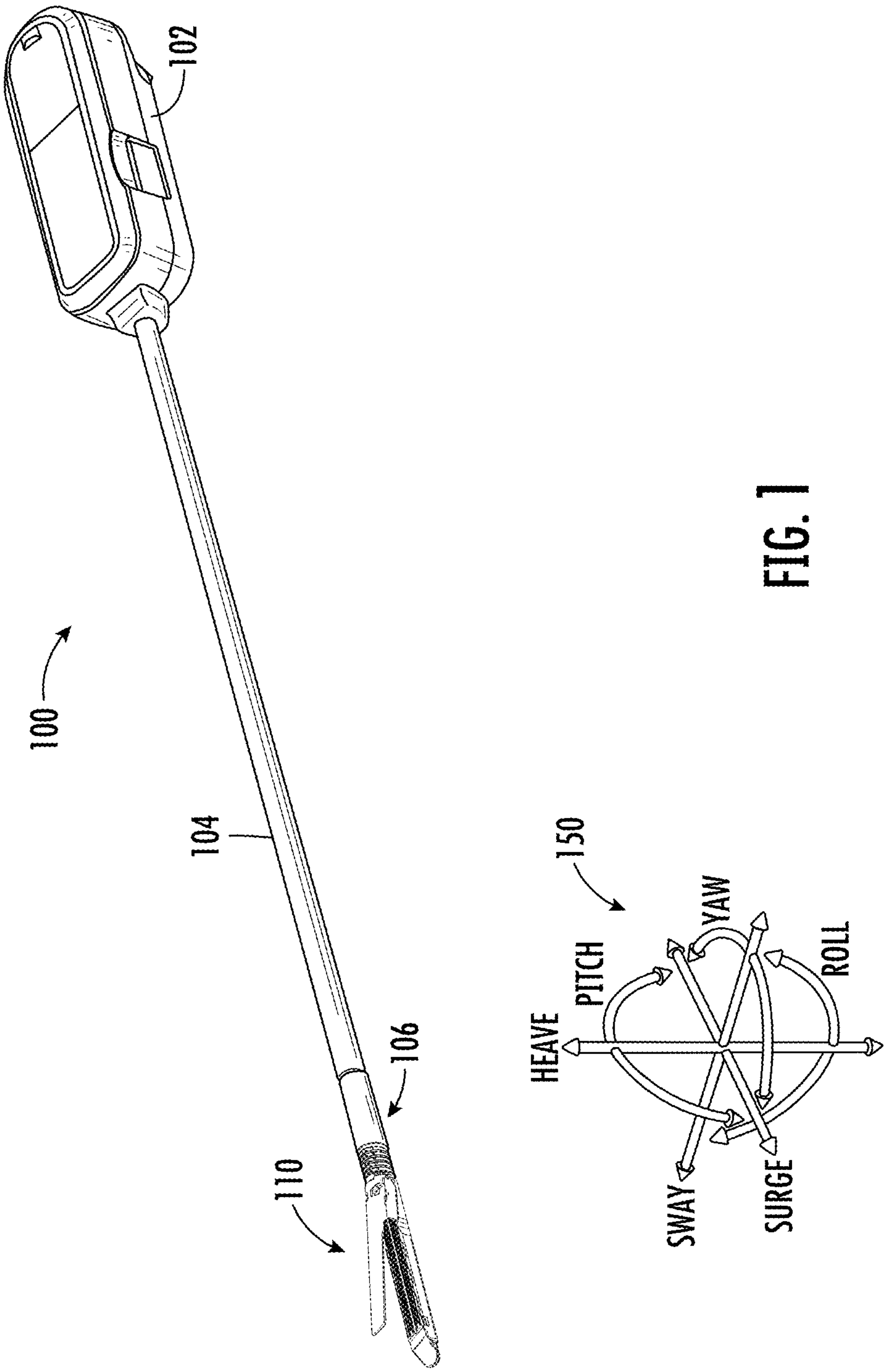
FIG. 1 is a perspective view of an embodiment of a surgical stapler configured for use with a robotic surgical system.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, et cetera, may be used throughout the specification in reference to the surgical instruments described herein as well as in reference to the patient's natural anatomy. Such terms have well-understood meanings in both the study of anatomy and the field of surgery. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

Portions of the disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a surgical stapler or "endocutter" 100 is configured for use in minimally invasive surgery (MIS) procedures including, but not limited to, endoscopic and laparoscopic procedures. The surgical stapler 100 is configured to contemporaneously transect and staple tissue during the performance of such surgical procedures. Although the concepts presented below are described in regard to a surgical stapler, it should be appreciated that the presented concepts may be applicable to other types of surgical instruments configured to perform different surgical functions including, but not limited to, surgical scissors, tissue graspers, energy-based surgical instruments, clip appliers, needle drivers, and/or other surgical instruments.

The illustrative surgical stapler 100 includes a drive housing 102, an elongated shaft 104 that extends distally away from the drive housing 102, and an end effector 110 located at a distal end of the elongated shaft 104 opposite the drive housing 102. As discussed in more detail below, the surgical stapler 100 is embodied as a robotic surgical stapler and is configured to be used with a corresponding robotic surgical system. As such, the drive housing 102 includes coupling features that that facilitate the mounting of the drive housing 102 to a robotic arm of a robotic manipulator of the robotic surgery system as discussed below in regard to FIGS. 8 and 9. The mounting of the drive housing 102 to the robotic arm allows the robotic manipulator to control various functions of the surgical stapler 100, including the movement and "firing" of the end effector 110, as discussed in more detail below.

The elongated shaft 104 is sized and configured for use in minimally invasive surgery procedures. For example, the elongated shaft 104 has a length and diameter that is sized to allow the elongated shaft 104 to be inserted into a trocar or similar surgical tube to allow positioning of the end effector 110 into the patient's anatomical environment (e.g., the patient's abdominal cavity). Illustratively, the distal end of the elongated shaft 104 is coupled to the end effector 110 via an articulable joint 106, which allows the end effector 110 to be moved to different orientations and/or positions relative to the elongated shaft 104.

In the illustrative embodiment, the articulable joint 106 provides six degrees of freedom to the end effector 110. For example, as indicated by coordinate frame 150, the degrees of freedom of the end effector 110 may include three translational degrees (i.e., surge, heave, and sway) and three rotational degrees (i.e., roll, pitch, and yaw). The "surge" degree of freedom refers to forward and backward translational movement of the end effector 110 relative to the elongated shaft 104, the "heave" degree of freedom refers to upward and downward translational movement of the end effector 110 relative to the elongated shaft 104, and the "sway" degree of freedom refers to left and right translational movement of the end effector 110 relative to the elongated shaft 104. The "roll" degree of freedom refers to rotation of the end effector 110 along a longitudinal axis defined by the end effector 110, the "pitch" degree of freedom refers to upward and downward tilting of the end effector 110 relative to the elongated shaft 104, and the "yaw" degree of freedom refers to leftward or rightward turning of the distal end of the end effector 110 relative to the elongated shaft 104.

The elongated shaft 104 also houses a portion of an actuation system (not shown) to control the movement and activation (e.g., the "firing") of the end effector 110. The actuation system may include various articulation cables, push rods, firing rods, and/or other devices, which extend through the elongated shaft 104 from mechanisms located in the drive housing 102 to components of the articulable joint 106 and/or the end effector 110. In this way, the drive housing 102 is configured to control the movement and activation (i.e., the "firing") of the end effector 110.

Figure 2:
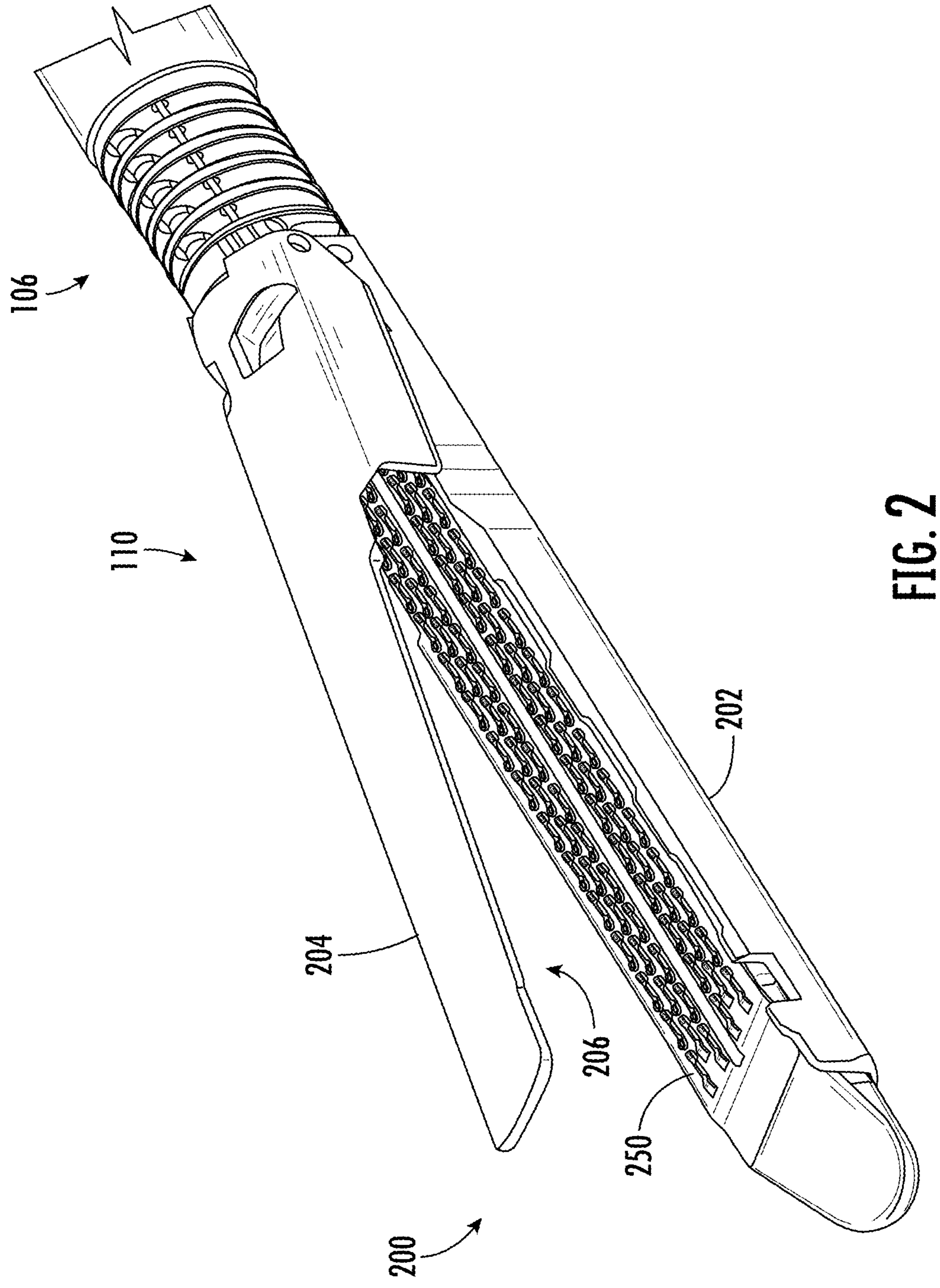
FIG. 2 is a perspective view of an embodiment of an end effector of the surgical stapler of FIG. 1.

Referring now to FIG. 2, the end effector 110 includes a jaw assembly 200, which illustratively includes a pair of jaws 202, 204 that oppose each other. The jaw 202 is illustratively embodied as a "cartridge" jaw and includes a channel 300 (see FIG. 3) configured to receive a staple cartridge 250. The jaw 204 is illustratively embodied as an "anvil" jaw and includes a bottom surface 206 having forming pockets configured to deform staples ejected from the staple cartridge 250.

The jaw assembly 200 is movable between an open state in which the anvil jaw 204 is positioned away from the cartridge jaw 202 and a closed state in which the anvil jaw 204 is positioned near or otherwise contacts the cartridge jaw 202. Illustratively, the anvil jaw 204 is configured to move toward and away from the cartridge jaw 202. However, in other embodiments, the cartridge jaw 202 may be configured to move relative to the anvil jaw 204 or both jaws 202, 204 may be configured to move toward or away from each other. Additionally, it should be appreciated that the open state may correspond to a degree of openness that is less than a fully opened position of the jaw assembly 200 and the closed state may correspond to a degree of closeness that is less than a fully closed position. That is, the closed state may, for example correspond to a minimal distance between the distal ends of the cartridge jaw 202 and the anvil jaw 204 and the open state may correspond to a maximum distance between the distal ends of the jaws 202, 204. However, in other embodiments, the open state may correspond to a fully opened position of the jaw assembly 200 and the closed state may correspond to a fully closed position of the jaw assembly 200.

Figure 3:
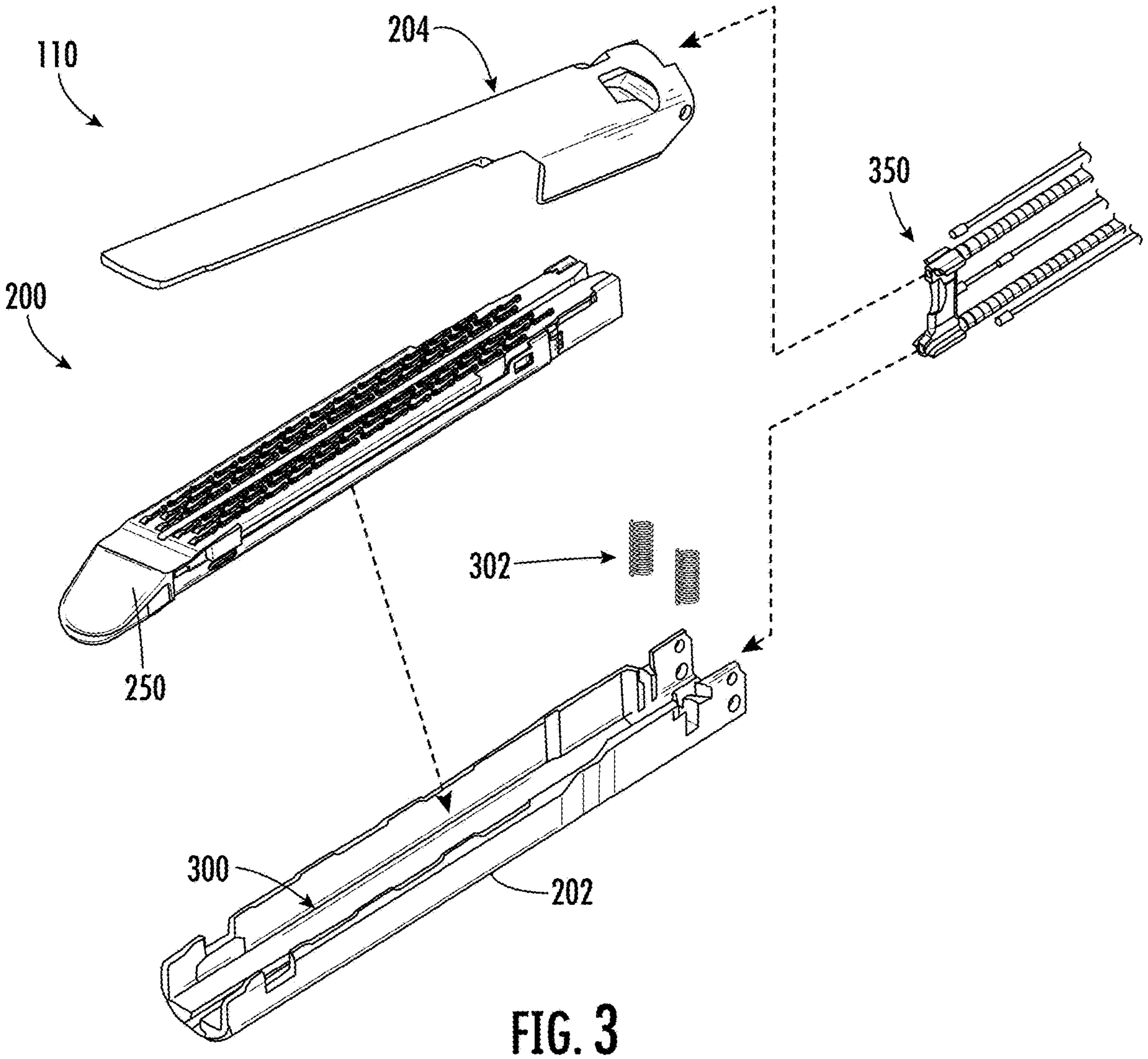
FIG. 3 is an exploded perspective view of and embodiment of a distal end of the surgical stapler of FIG. 1, including the end effector of FIG. 2.

As shown in FIG. 3, the jaw assembly 200 is biased in the open state by a pair of springs 302. That is, the springs 302 bias the anvil jaw 204 away from the cartridge jaw 202.

However, actuation of the jaw assembly 200 overcomes the biasing force of the springs 302 to move the jaw assembly 200 from the open state to the closed state. When in the closed state, the end effector 110 can be "fired" to effect the cutting and stapling of tissue held within the jaw assembly 200

The end effector 110 also includes an I-beam 350, which is configured to translate forward during the firing of the end effector 110 from the proximal end of the jaws 202 toward the distal end of the jaws 202, 204. To do so, portions of the I-beam 350 are received in corresponding channels of the cartridge jaw 202 and the anvil jaw 204 as discussed in more detail below in regard to FIGS. 4 and 5. When the end effector 110 is fired, the I-beam 350 translates forward within the channels of the jaws 202, 204. The forward movement of the I-beam 350 may cause the anvil jaw 204 to move further downward toward or against the cartridge jaw 202 and clamp the jaw assembly in the closed state.

Figure 5:
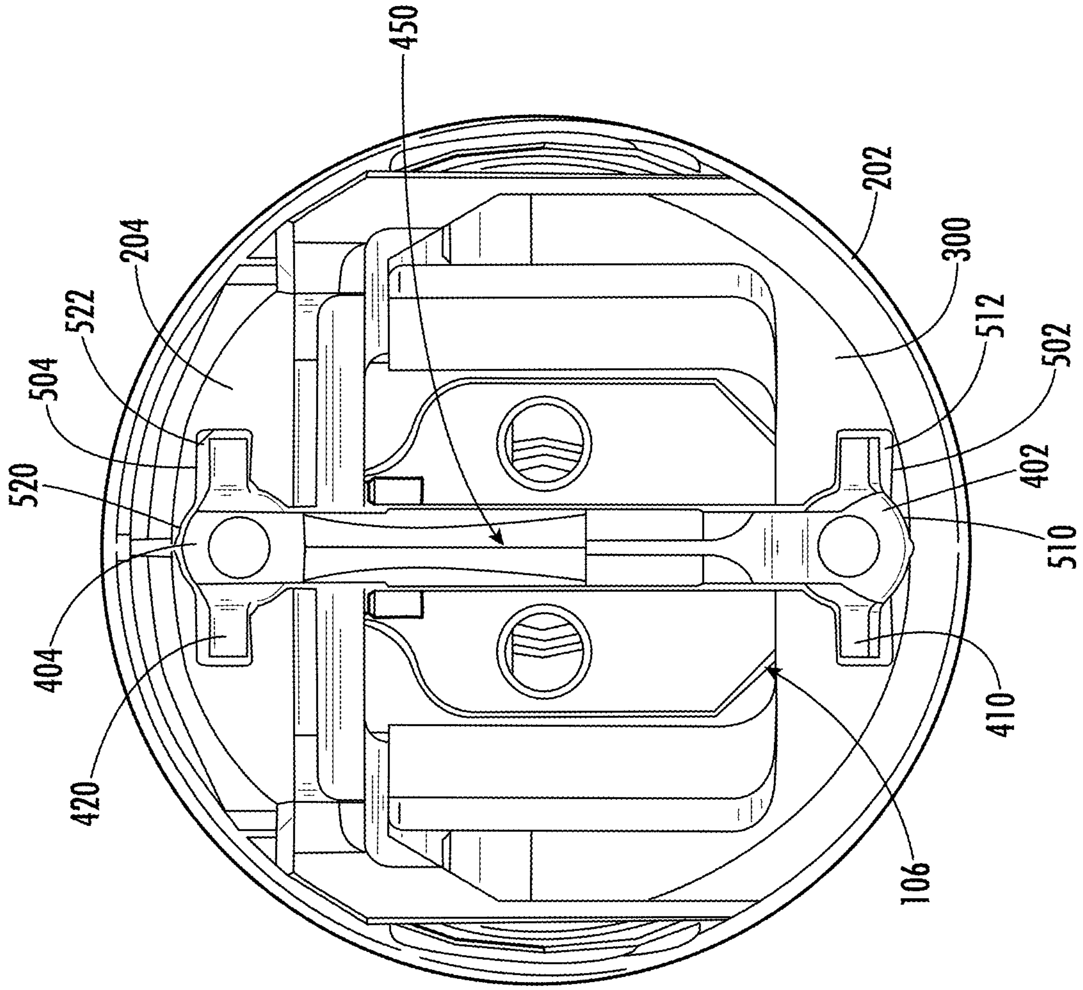
FIG. 5 is a cross-sectional view of the end effector of FIG. 1 in a closed state and showing the I-beam of FIG. 4 received in corresponding channels of the end effector of FIG. 2 with the knife of the I-beam extending between the corresponding channels.
Figure 4:
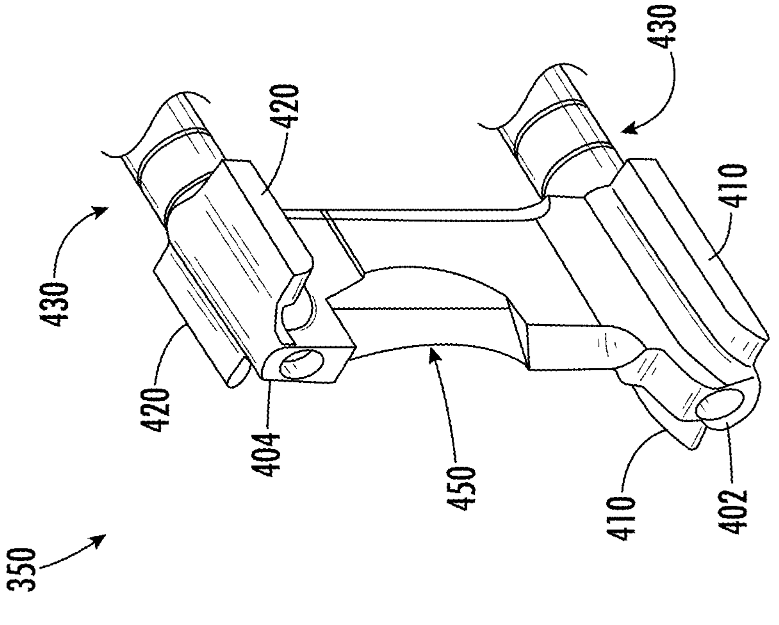
FIG. 4 is a perspective view of an embodiment of an I-beam of the end effector of FIG. 2, which includes a knife.

Referring now to FIGS. 4 and 5, the I-beam 350 includes a lower base 402, an upper base 404, and a knife 450 located between the upper and lower bases 402, 404. A pair of lower wings 410 extend laterally outward from the lower base 402. Similarly, a pair of upper wings 420 extend laterally outward from the upper base 404. A push rod 430 is coupled to each of the bases 402, 404 and to control mechanisms located in the drive housing 102. The control mechanisms of the drive housing 102 control movement of the push rods 430, which move the I-beam 350 forward and backward within the jaw assembly 200.

When the end effector 110 is fired, I-beam 350 moves within a lower I-beam channel 502 of the cartridge jaw 202 and an upper I-beam channel 504 of the anvil jaw 204 as shown in FIG. 5. The I-beam channel 502 of the cartridge jaw 202 includes a base channel 510 and a pair of wing channels 512, which are open to and in fluid communication with the base channel 510 and extend laterally outward therefrom. The lower base 402 of the I-beam 350 is received in and moves within the base channel 510 of the I-beam channel 502. Similarly, each lower wing 410 is received in and moves within a corresponding one of the wing channels 512. The I-beam channel 504 of the anvil jaw 204 also includes a base channel 520 and a pair of wing channels 522, which are open to and in fluid communication with the base channel 520 and extend laterally outward therefrom. The upper base 404 of the I-beam 350 is received in and moves within the base channel 520 of the I-beam channel 502. Similarly, each upper wing 420 is received in and moves within a corresponding one of the wing channels 522.

Figure 6:
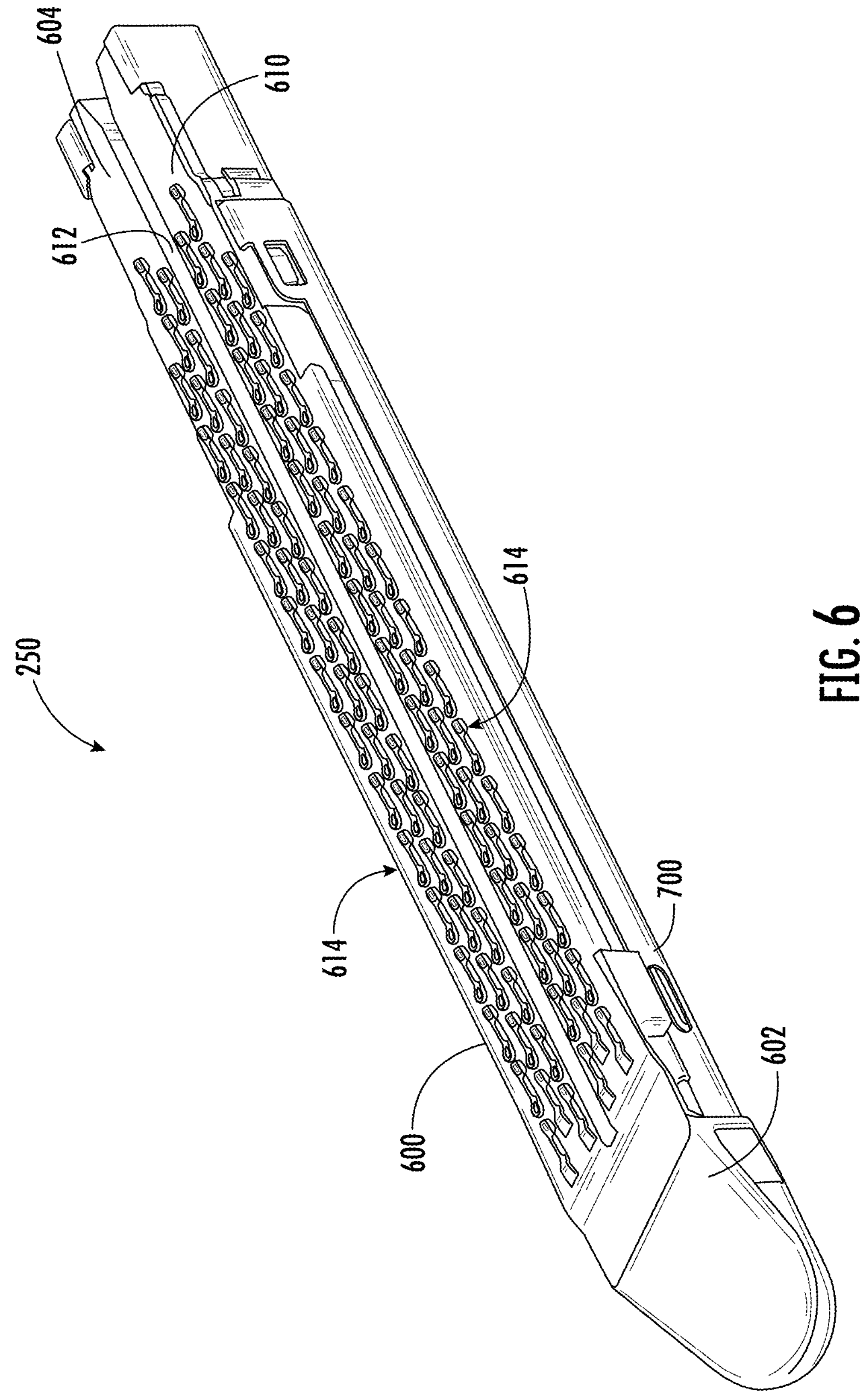
FIG. 6 is a perspective view of an embodiment of a stapler cartridge that may be inserted into the end effector of FIG. 2.
Figure 7:
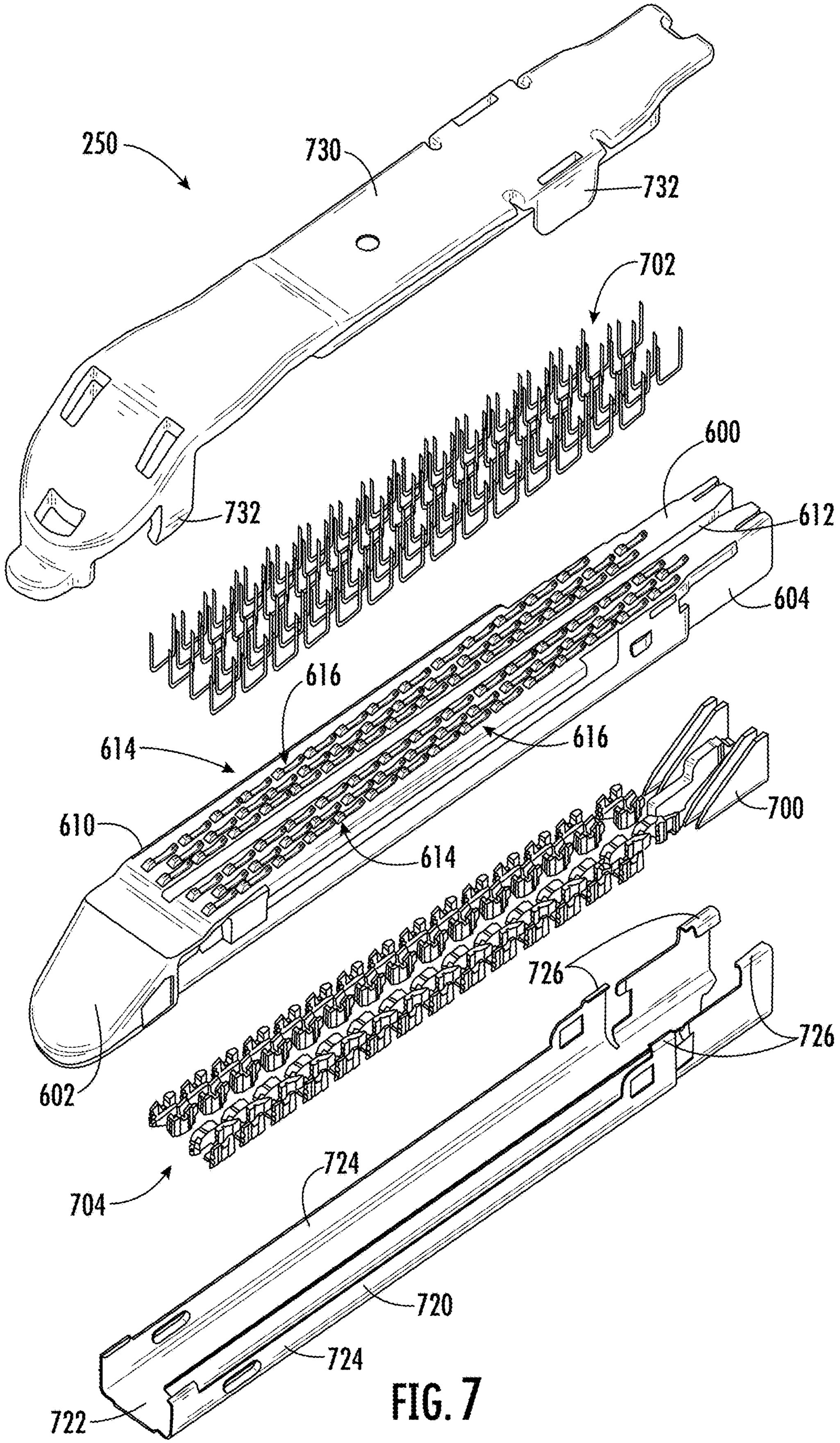
FIG. 7 is an exploded, perspective view of the stapler cartridge of FIG. 6.

Referring now to FIGS. 6 and 7, the illustrative staple cartridge 250 includes a cartridge body 600 having a distal end 602 and a proximal end 604. The cartridge body 600 also includes a deck 610 that extends from the proximal end 604 to the distal end 602. The deck 610 includes a longitudinal knife slot 612 that is located centrally on the deck 610 and extends from the distal end 602 toward the proximal end 604 of the cartridge body 600. During a firing stroke of the surgical stapler 100 (i.e., when the end effector is "fired"), the I-beam 350 transversed along the longitudinal knife slot 612 with the knife 450 of the I-beam 350 protruding upwardly from the longitudinal knife slot 612 to facilitate the transection of tissue captured within in the end effector 110 and held between the staple cartridge 250 and the anvil jaw 204.

A set of staple cavities 614 are defined in the deck 610 on either side of the longitudinal knife slot 612. A staple 702 is positioned in each of the staple cavities 614 and is supported by a corresponding staple driver 704. The staple cartridge 250 also includes a staple sled 700, which is initially located toward the proximal end 604 of the cartridge body 600 and is pushed toward the distal end 602 by the I-beam 350 when the end effector 110 is fired. The staple sled 700 lifts each staple driver 704 when the sled 700 comes into contact with the corresponding staple driver 704, which ejects the staple 702 associated with the corresponding staple driver 704 from the corresponding staple cavity 614. In the illustrative embodiment, the deck 610 includes staple guides or projections 616 that project upwardly from the deck 610 around each staple cavity 614. The staple guides 616 are configured to guide or control the legs of the staples 702 as the staples 702 are being ejected from the staple cavities 614. Illustratively, the staple guides 616 are located around the distal and proximal ends of each staple cavity 614, but may completely surround each staple cavity 614 or be located on only one end of each staple cavity 614 in other embodiments. The staple guides 616 may also form a set of "teeth" and be configured to grasp tissue held within the jaw assembly 200 to restrict movement of the tissue. In other embodiments, the deck 610 of the cartridge body 600 maybe devoid of any staple guides 616.

The staple cartridge 250 also includes a pan 720, which is attached to the cartridge body 600 and is configured to retain the staple drivers 704 and associated staples 702 within the cartridge body 600. Illustratively, the pan 720 is formed from a metallic material and includes a floor 722 and a pair of sidewalls 724 that extend upwardly from the floor 722 and wrap onto the sides of the cartridge body 600. The pan 720 includes a set of attachment tabs 726 that are configured to secure the pan 720 to the cartridge body 600.

Prior to use, the staple cartridge 250 includes a cover 730 attached to the cartridge body 600. The cover 730 is configured to cover the deck 610 of the staple cartridge 250 and includes a set of attachment tabs 732 configured to secure the cover 730 to the cartridge body 600. To prepare the staple cartridge 250 for use in the end effector 110, the cover 730 is removed from the cartridge body 600.

Although not illustrated in FIGS. 6 and 7, the staple cartridge 250 may also includes one or more electronic circuits or devices configured to perform one or more associated functions. For example, such electronic circuitry may include processors, digital storage devices, communication circuitry, sensor circuitry, and/or other electrical components.

Figure 8:
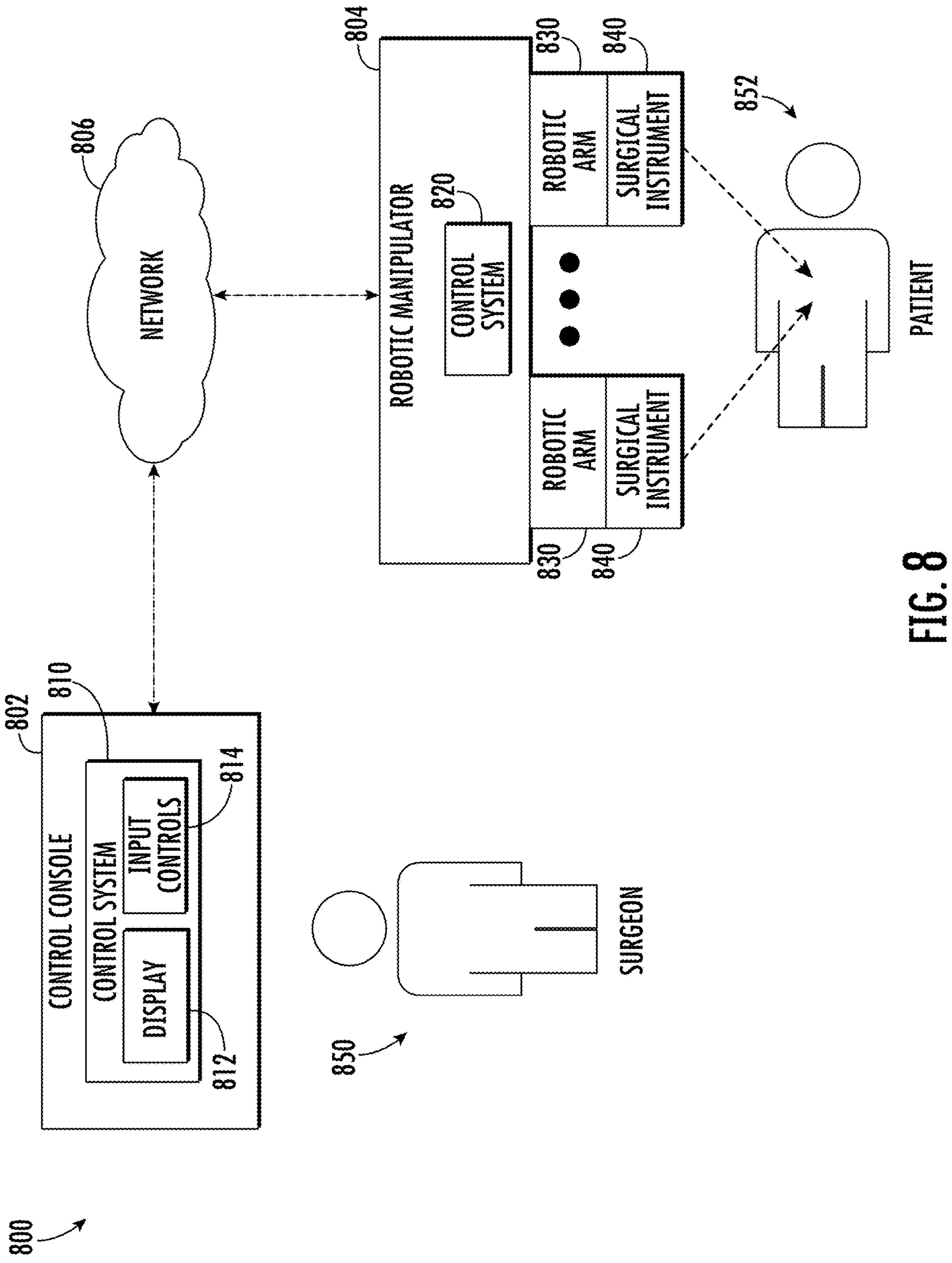
FIG. 8 is a simplified block diagram of an embodiment of a robotic surgical system including a control console and a robotic manipulator, with which the surgical stapler of FIG. 1 may be used.

Referring now to FIG. 8, as discussed above, the illustrative surgical stapler 100 is configured for use with a corresponding robotic surgical system 800. The robotic surgical system 800 includes a control console 802 and a robotic manipulator 804, which communicate with each other over a communication network 806. Although only a single control console 802 and a single robotic manipulator 804 is shown in FIG. 8, it should be appreciated that the robotic surgical system 800 may include additional control consoles 802 and/or robotic manipulators 804 in other embodiments.

The control console 802 is usable by a surgeon 850 to control the operation of the robotic manipulator 804. To do so, the control console 802 includes a control system 810. Illustratively, the control system 810 includes a display 812 and one or more input controls 814. However, it should be appreciated that the control system 810 may include additional electrical components and devices, such as a processor, a memory, and a communication subsystem to enable communications of the components of the control system 810, which are not illustrated in FIG. 8 for clarity.

The display 812 may be embodied as any type of display device capable of generating images viewable by the surgeon 850. In use, the display 812 may display images related to the surgical procedure being performed via the robotic manipulator 804. The displayed images may be obtained from, for example, an endoscopic camera operated by the robotic manipulator 804. Additionally, the display 812 may display information, including data determined by the control console 802 and/or the robotic manipulator 804, related to the surgical procedure (e.g., positional data of the robotic manipulator 804).

The input controls 814 are usable by the surgeon 850 to control the functionality of the robotic manipulator 804. The input controls 814 may be embodied as any type of input device capable of receiving a corresponding input from the surgeon 850. For example, the input controls 814 may include physical controllers, such as joy sticks, hand-held actuator modules, exoskeletal gloves, and/or other input devices. The input controls 814 may also include input devices other than hand-controlled devices such as foot pedals, vison tracking modules, and/or the like. In many embodiments, the input controls 814 are movable in multiple degrees of freedom to control the positioning and operation of the robotic manipulator 804.

The robotic manipulator 804 also includes a control system 820 and one or more robotic arms 830 to which surgical instruments 840 (e.g., the surgical stapler 100) may be mounted. In some embodiments, the robotic manipulator 804 may be mounted to a transport cart, sometimes referred to as an "arm cart," that enables mobility of the robotic manipulator 804 and the associated robotic arms 830.

The robotic arms 830 may include various articulable linkages and associated motors, which are controllable by the control console 802 to move the corresponding robotic arm 830 and any associated surgical instrument 840 to a desired position. For example, by manipulating an input control 814 of the control console 802, the surgeon 850 may control the positioning of a corresponding robotic arm 830, as well as the functionality of the associated surgical instrument 840 (e.g., the firing of the surgical stapler 100).

The control system 820 may be embodied as any type of controller or control circuit capable of controlling the functionality of the robotic manipulator including, for example, the movement of the robotic arms 830 and the activation of the surgical instruments 840 based on control signals received from the control console 802. To do so, the control system 820 may include various electrical components, circuits, and/or devices, such as a processor, a memory, and a communication subsystem to enable communications of the components of the control system 820, which are not illustrated in FIG. 8 for clarity.

In use, the robotic manipulator 804 is positioned in close proximity to a patient 852 requiring surgery. The robotic manipulator 804 may be locked or mounted in place for the duration of the surgery. The surgeon 850 may then manipulate the input controls 814 to position one or more robotic arms 830 and associated surgical instruments 840 into a desired position. For example, the surgeon 850 may position a robotic arm 830 such that an associated surgical instrument 840 is inserted through a trocar or similar elongated passageway into the anatomical environment (e.g., the abdominal cavity of the patient 852). Once so positioned, some surgical instruments 840 (e.g., an endoscope) may be locked into position to avoid unintended repositioning.

The network 806 may be embodied as any type of wired and/or wireless network or set of communication links capable of facilitating communications between the control console 802 and the robotic manipulator 804. To do so, the network 806 enable such communications using any suitable data communication specification and/or protocol. As such, in some embodiments, the network 806 may include additional devices, such as additional computers, routers, stations, and/or switches, to facilitate such communications between the control console 802 and the robotic manipulator 804.

Figure 9:
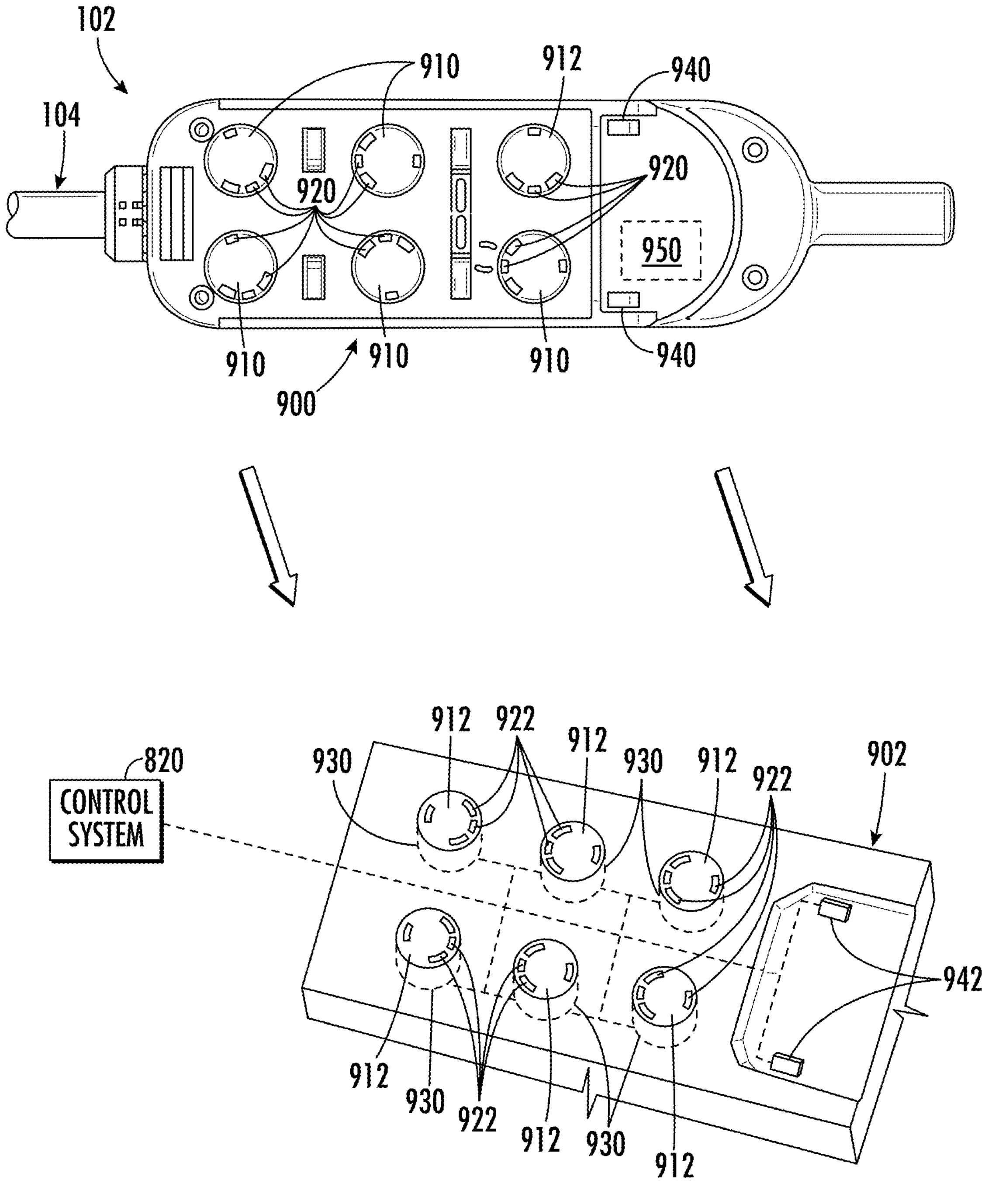
FIG. 9 is a diagrammatic view of an embodiment of a tool interface located on a bottom side of a drive housing of the surgical stapler of FIG. 1 being coupled to an arm interface located on a robotic arm of the robotic manipulator of the robotic surgical system of FIG. 8.

Referring now to FIG. 9, as discussed above, the surgical stapler 100 (and other surgical instruments 840) is configured to be mounted to a robotic arm 830 of the robotic manipulator 804. To facilitate such mounting, the drive housing 102 of the surgical stapler 100 includes a tool interface 900 located on a bottom side of the drive housing 102. The tool interface 900 is configured to mate with an arm interface 902 of the corresponding robotic arm 830 to couple the surgical stapler 100 to the robotic arm 830. The coupling of the surgical stapler 100 to the robotic arm 830 may be further facilitated via various mechanical, magnetic, and/or electrical features. In some embodiments, a sterile barrier may also be used between the surgical stapler 100 and the robotic arm 830. It should be appreciated that mounting of the surgical stapler 100 to the robotic arm places the surgical stapler 100 into communication and under the control of the control system 820 of the robotic manipulator 804, which is controlled by the control console 802 as discussed above.

The tool interface 900 includes a set of input pucks 910, which are manipulable to control functions of the surgical stapler 100 such as the positioning and firing of the end effector 110. Each input puck 910 is configured to mate with a corresponding puck driver 912 of the arm interface 902. To do so, each input puck 910 includes mating features 920 that are configured to mate with mating features 922 of the corresponding puck driver 912. In the illustrative embodiment, the mating features 920 of the input pucks 910 are embodied as tabs or protrusions that extend upwardly from the corresponding input puck 910, and the mating features 922 of the puck drivers 912 are embodied as recesses configured to receive the tabs/protrusions 920 of the input pucks 910. In other embodiments, however, the mating features 920 of the input pucks 910 may be embodied as recesses and the mating features 922 of the puck drivers 912 may be embodied as tabs/protrusions.

The arm interface 902 includes an electric motor 930 operatively coupled to each puck driver 912. Each electric motor 930 is communicatively coupled to and controlled by the control system 820. Actuation of a given electric motor 930 causes actuation of the associated puck driver 912, which causes actuation of the corresponding input puck 910. For example, rotation of an electric motor 930 causes rotation of the associated puck driver 912, which causes rotation of the corresponding input puck 910. In this way, the positioning and activation (e.g., "firing") of the end effector 110 of the surgical stapler 100 may be controlled via actuation of the puck drivers 912 and associated input pucks 910.

The tool interface 900 also includes a set of electrical connectors 940, which are configured to mate with corresponding electrical connectors 942 of the arm interface 902. The electrical connectors 940, 942 provide electrical communication between the surgical stapler 100 and the robotic manipulator 804. However, in other embodiments, the surgical stapler 100 and the robotic manipulator 804 may be configured to communicate in other ways, such as via wireless communications. In some embodiments, the tool interface 900 may also include a control system 950. In such embodiments, the control system 950 may be configured to control and/or monitor various operations the surgical stapler 100. The control system 950 may include various electrical components, circuits, and/or devices, such as a processor, a memory, and a communication subsystem to enable communications of the components of the control system 950, which are not illustrated in FIG. 9 for clarity.

Figure 10:
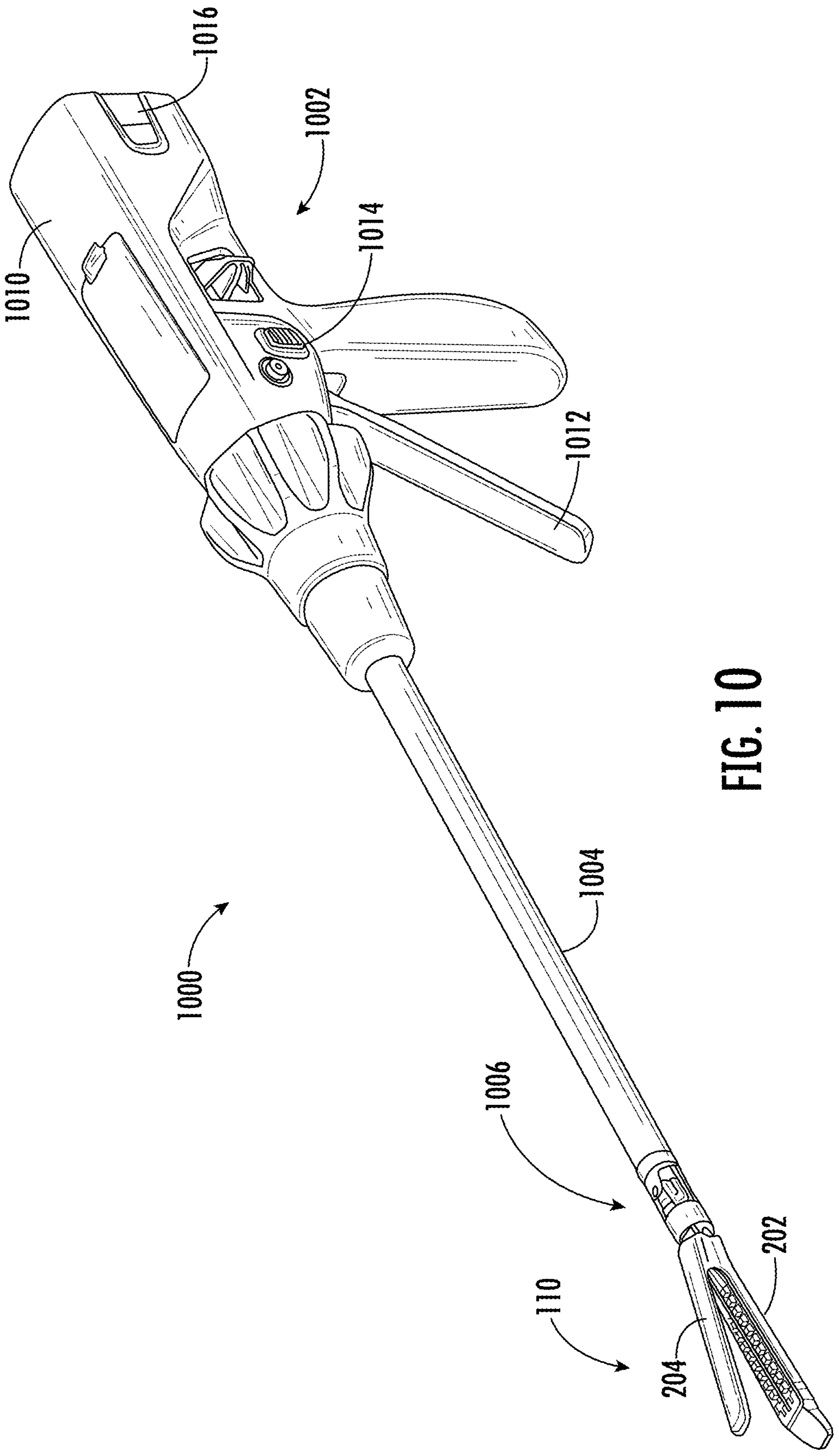
FIG. 10 is a perspective view of an embodiment of a hand-held surgical stapler including the end effector of FIG. 2.

Although the illustrative surgical stapler 100 shown and described above in regard to FIGS. 1-9 is configured for use in a robotic surgical system, the features and concepts of the surgical stapler 100 described above and below may be applicable to hand-held surgical staplers and devices. For example, as shown in FIG. 10, the end effector 110 may be incorporated into a hand-held surgical stapler 1000. The surgical stapler 1000 includes a handle 1002 and an elongated shaft 1004 extending from the handle 1002. The distal end of the elongated shaft 1004 is coupled to the end effector 110 via an articulable joint 1006, which may be substantially similar to the articulable joint 106 described above.

The handle 1002 includes a handle housing 1010 and a trigger assembly 1012 movable connected to the handle housing 1010. The trigger assembly is operable by a surgeon to move the jaw assembly 200 of the end effector 110 from the open state to the closed state as discussed above. The handle 1002 also includes one or more activation triggers 1014 to, for example, initiate the firing of the end effector 110 when in the closed state. A replaceable and/or rechargeable battery pack 1016 is coupled to an end of the handle housing 1010 and provide power to the electrical components located within the handle housing 1010.

Figure 11:
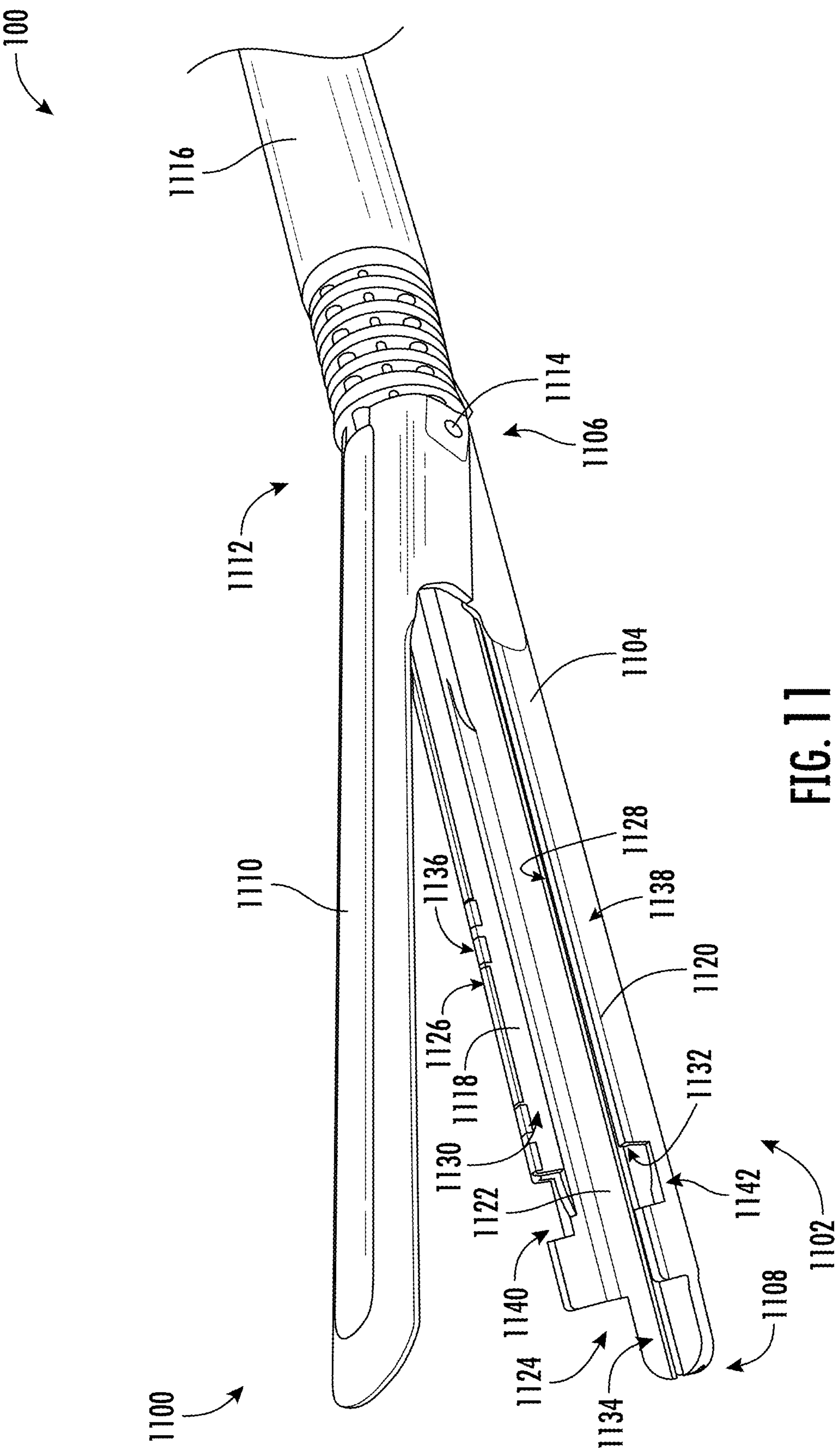
FIG. 11 is a perspective view of an end effector for a surgical instrument.
Figure 12:
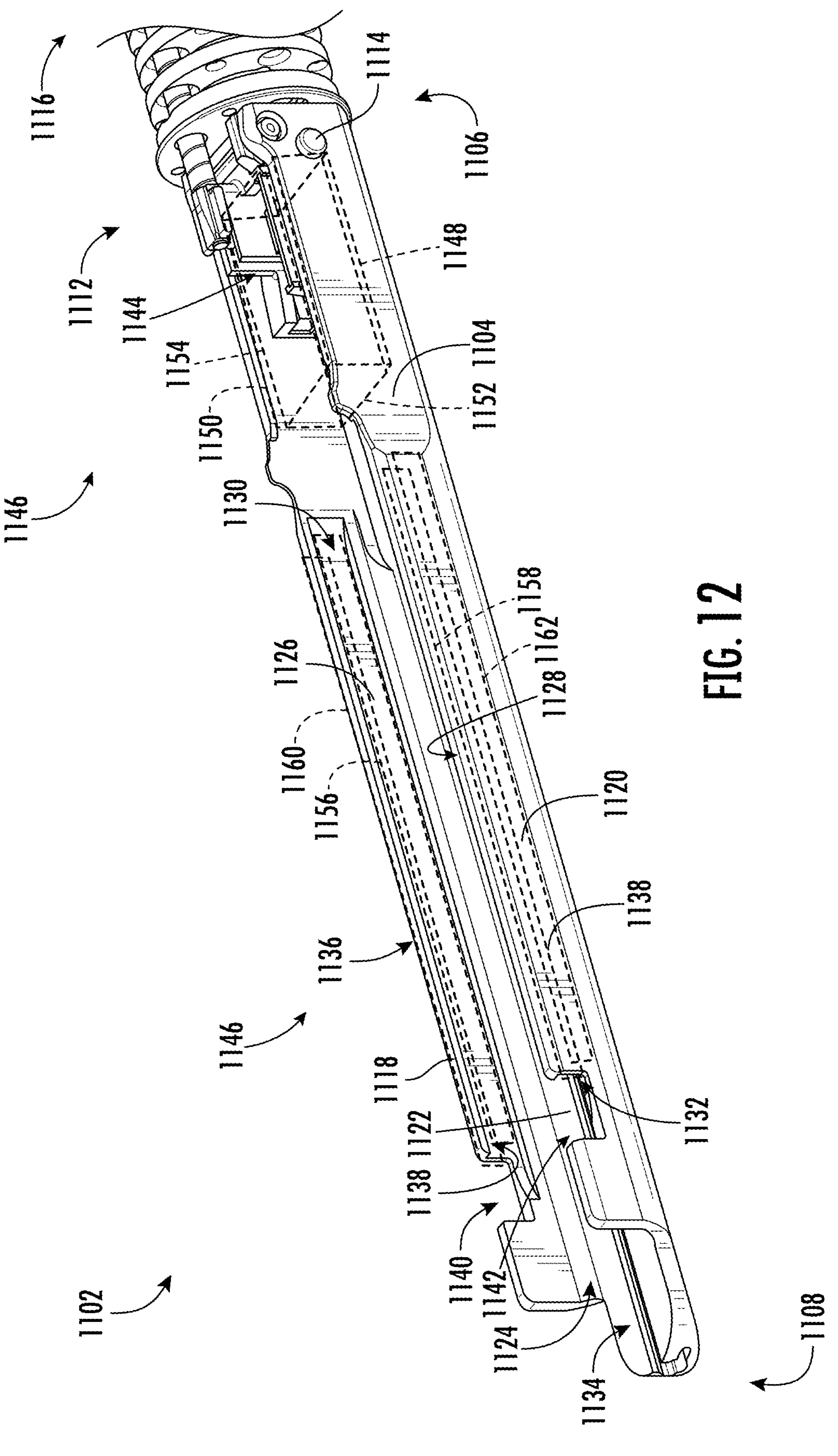
FIG. 12 is a perspective view of a lower jaw of the end effector of FIG. 11.

Referring now to FIGS. 11-12, in an illustrative embodiment, the end effector 110 of the surgical stapler 100 and/or the hand-held surgical stapler 1000 may be embodied as an end effector 1100 having a cartridge jaw 1102 including an elongated body 1104 that extends from a proximal end 1104 to a distal end 1106. The illustrative end effector 1100 may be similar to an end effector 110 of the surgical stapler 100 and/or the hand-held surgical stapler 1000, and thus may include one or more components similar to the end effector 110 as described above.

Illustratively, the cartridge jaw 1102 is coupled to an anvil jaw 1110 at a hinge 1112 by a pin 1114. A shown, the hinge 1112 is positioned toward the proximal end 1106 of the cartridge jaw 1102. Accordingly, and as described further below, the anvil jaw 1110 may pivot about the pin 1114 and rotate from an open position as shown in FIG. 11 to a closed position in which the anvil jaw 1110 contacts the cartridge jaw 1102, grasps tissue between the anvil jaw 1110 and the cartridge jaw 1102, and/or comes near the cartridge jaw 1102.

As shown, the proximal end 1106 of the cartridge jaw 1102 is further coupled to a shaft 1116, which may be coupled to a robotic tool interface of the surgical stapler 100 and/or a handpiece of the hand-held surgical instrument 1000, as described above. Accordingly, the shaft 1116 further includes a drivetrain for actuating the end effector 1100, such as a spring driveshaft, one or more pushrods, shafts, and/or other actuators.

As shown, the cartridge jaw 1102 includes a pair of parallel, opposing side walls 1118, 1120 that extend from the hinge 1112 toward the distal end 1108. A floor 1122 connects the side walls 1118, 1120, and extends from the hinge 1112 to the distal end 1108. The side walls 1118, 1120 and the floor 1122 cooperate to define a channel 1124, which also extends from the hinge 1112 to the distal end 1108.

Each of the side walls 1118, 1120 includes a respective inner surface 1126, 1128 that faces the channel 1124. A pair of grooves 1130, 1132 are respectively defined in the inner surfaces 1126, 1128. Accordingly, each of the grooves 1130, 1132 is in communication with the channel 1124.

A slot 1134 is defined in the floor 1122 and extends from the proximal end 1106 to the distal end 1108 of the cartridge jaw 1102. Illustratively, the slot 1134 may be formed by a pair of parallel slot walls extending downward from the floor 1122. Each of those walls curve together, forming a closed floor of the slot 1134. As shown, the slot 1134 is in communication with the channel 1124. As described further below, the slot 1134 is configured to receive the I-beam 350 of the end effector 1100. Accordingly, in some embodiments, the walls may further form one or more side annexes, depressions, or other curved features below the floor 1122, which may receive features of the I-beam 350, such as a lower beam or wing 410.

Although illustrated in FIG. 11 as including a pair of grooves 1130, 1132 defined in the respective side walls 1118, 1120, it should be understood that in other embodiments the end effector 1100 may include a different number and/or arrangement of grooves defined in the side walls 1118, 1120 and/or the floor 1122. For example, in an embodiment, the cartridge jaw 1102 may be asymmetric, with a groove 1130 defined in the side wall 1118, but without a groove 1132 defined in the side wall 1120. Similarly, in another embodiment, the cartridge jaw 1102 may include a groove 1132 defined in the side wall 1120 but may be without the groove 1130 defined in the side wall 1118. Additionally or alternatively, as shown in FIG. 11, each of the side walls 1118, 1120 further includes a respective outer side surface 1136, 1138, and in some embodiments, one or more grooves may be defined in the outer surfaces 1136, 1138. Those grooves defined in the outer surfaces 1136, 1138 may be in addition to and/or in alternative to one or more of the grooves 1130, 1132 defined in the inner surfaces 1126, 1128. Additionally or alternatively, in some embodiments, one or more grooves may be defined in the floor 1122, on either side of the knife slot 1134.

Additionally, in some embodiments, a distance between the outer side surfaces 1136, 1138 may be constrained to fit within the dimensions of pre-existing surgical instruments, for example to fit within a standardized trocar or other aperture used with surgical instruments. Accordingly, the end effector 1100 may be used as an improved replacement for existing end effectors in surgical instruments.

In use, and as described further below, a staple reload cartridge (not shown) may be mounted to the end effector 1100 for use in a surgical stapling operation, also called a firing of the instrument 102. The cartridge may be attached to the end effector 1100 by being inserted into the channel 1124 of the cartridge jaw 1102. The cartridge jaw 1102 illustratively includes a pair of notches 1140, 1142 that are further defined in the respective side walls 1118, 1120. In some embodiments, the notches 1140, 1142 may receive corresponding keys of a staple reload cartridge, allowing the cartridge to be easily positioned within the cartridge jaw 1102.

When the reload cartridge is inserted in the end effector 1100 and prior to a firing operation, the I-beam 350 is positioned proximally from the cartridge, within a cavity 1144 defined within the cartridge jaw 1102. In particular, the side walls 1118, 1120 and the floor 1122 cooperate to define the cavity 1144 toward the proximal end 1106 of the cartridge jaw 1102. As shown, the pin 1114 of the hinge 1112 passes through the cavity 1144, attaching the anvil jaw 1110 to the cartridge jaw 1102. In some embodiments, the I-beam 350 may be prevented from moving proximally out of the cartridge jaw 1102 by the pin 1114. The slot 1134 extends to the cavity 1144, which may allow a lower beam 410 or other feature of the I-beam 350 to enter the slot 1134 during the firing operation.

During the firing operation, the handpiece and/or robotic tool interface causes the drivetrain to move a I-beam 350 of the end effector 1100 from the proximal end 1104 to the distal end 1106. As the I-beam 350 moves distally, the I-beam 350 exits the cavity 1144, an upper beam or wing 420 is received in a slot defined in the anvil jaw 1110 and the lower beam 410 is received in the slot 1134. As the I-beam 350 continues to move distally, the upper beam 420 urges the anvil jaw 1110 to swing closed, towards the cartridge jaw 1102. As the anvil jaw 1110 closes, tissue may be clamped between the deck of the cartridge and the anvil jaw 1110.

As the I-beam 350 moves distally, it pushes against a sled of the cartridge and also causes the sled to move distally. As the sled moves distally, it sequentially forces internal drivers upwards, which causes surgical staples to be ejected upward toward the anvil jaw 1110. As the staples bear against the anvil jaw 1110, they are bent into a shape that clamps the tissue that is currently between the deck and the anvil jaw 1110. Bending the staples into shape and clamping that tissue achieves hemostasis. After the sled 1482 has passed the tissue and hemostasis has been achieved, a knife 450 carried by the I-beam 350 cuts (transects) the tissue. This stapling and cutting operation may proceed for the entire length of the deck of the cartridge.

As shown in FIG. 12, the cartridge jaw 1102 includes multiple board positions 1146, each of which is a potential mounting location for a circuit board, electronic component, or related components. Illustratively, a pair of side positions 1148, 1150, a bottom position 1152 and a top position 1154 surround the proximal cavity 1144. As described further below, those board positions 1148, 1150, 1152, 1154 may surround the I-beam 350 when it is located in a stored, pre-firing position within the proximal cavity 1144. Additionally, in some embodiments, one or more inner groove board positions 1156, 1158 may be located within the respective grooves 1130, 1132 defined in the inner surfaces 1126, 1128 of the side walls 1118, 1120 of the cartridge jaw 1102. Similarly, in some embodiments, one or more outer groove board positions 1160, 1162 may be located on respective outer surfaces 1136, 1138 of the cartridge jaw 1102. As described further below, in embodiments, circuit boards, antennas, magnets, connectors, and/or other electronic components may be located in one or more of those board positions 1146.

Figure 13:
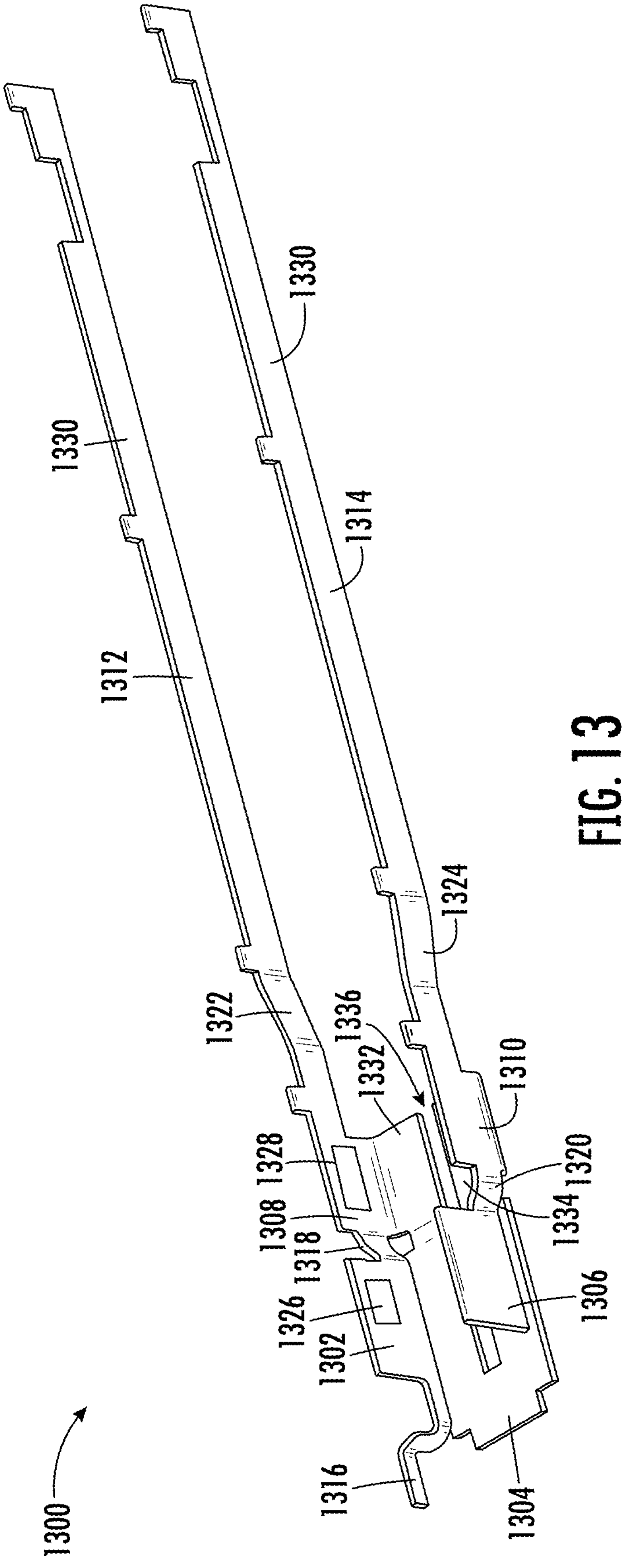
FIG. 13 is a perspective view of an electronics system that may be included in an end effector of FIGS. 11-12.
Figure 14:
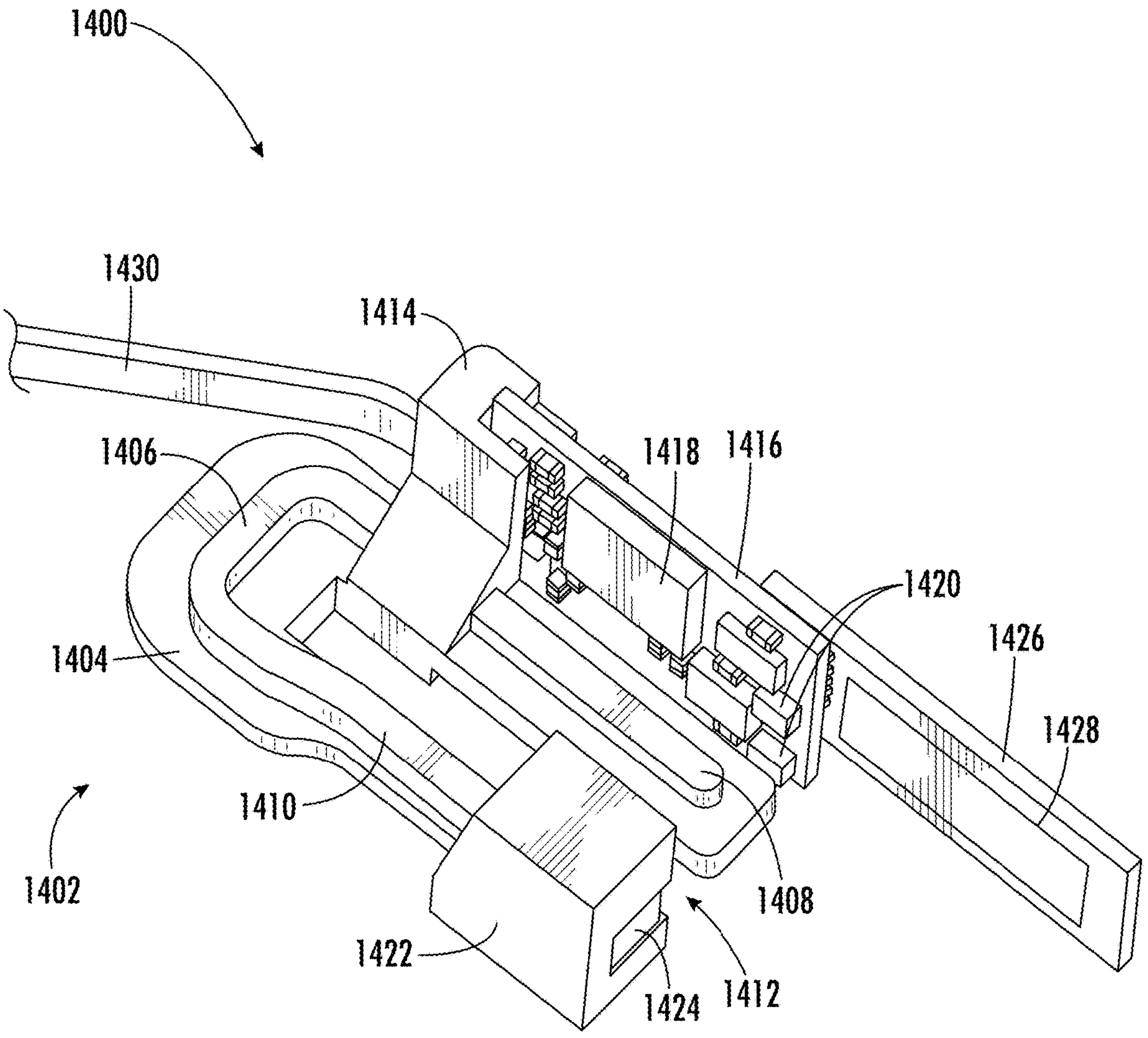
FIG. 14 is a perspective view of another embodiment of an electronics system that may be included in an end effector of FIGS. 11-12.

Referring now to FIG. 13, one potential embodiment of an electronics system 1300 that may be included in an end effector 1100 of a surgical stapler 100 as shown in FIGS. 11-12. The illustrative electronics system 1300 includes a main board 1302, which may be located at the side board position 1152. The system 1300 further includes a bottom board 1304 coupled to the main board 1302, which may be located at the bottom board position 1152. The system 1300 further includes a side board 1306 coupled to the bottom board 1304 and positioned in the side board position 1150, opposite the main board 1302. The illustrative system 1300 further includes additional side boards 1308, 1310 coupled to the main board 1302 and the side board 1306, respectively. The illustrative system 1300 further includes a pair of channel boards 1312, 1314 which are coupled to the additional side boards 1308, 1310 respectively, and are illustratively positioned in the inner groove board positions 1156, 1158, respectively. Each of those circuit boards of the electronics system 1300 may be embodied as any combination of one or more rigid circuit boards, flexible circuit boards, or other associated electronic components.

In the illustrative embodiment, the main board 1302 is coupled to additional electronics of the surgical stapler 100 (not shown) via a flex connector 1316, which may extend through a shaft of the instrument 102 to a handpiece, robotic adapter, or other component of the surgical stapler 100. Similarly, the circuit boards of the electronic system 1300 are electrically coupled together by flex connectors 1318, 1320, 1322, 1324. Additionally or alternatively, the components of the electronics system 1300 may be electrically coupled by a different number and/or arrangement of flex connectors, cables, connectors, or other electronic components.

Each of the circuit boards and other components of the electronics system 1300 may include one or more electronic components, including processors, controllers, sensors, antennas or other communications components, and any other appropriate electronic component. For example, in the illustrative embodiment, the main board 1302 includes a processor/controller 1326, the side boards 1308, 1310 may each include one or more antennas 1328 or other communication components, and the channel boards 1312, 1314 each include tissue sensors 1330 such as capacitance sensors and/or impedance sensors. Of course, in other embodiments different arrangements, numbers, and/or configurations of electronic components may be included in the electronics system 1300. For example, in embodiments, any of the circuit board positions shown in FIGS. 12 and 13 may be used for a main board and/or may include components of a main board such as the processor/controller 1326.

As described above, when the electronics system 1300 is coupled to the end effector 1100, the main board 1302, the bottom board 1304, and the side board 1306 surround the proximal cavity 1144 defined in the cartridge jaw 1102. Additionally, the bottom board 1304 illustratively includes a pair of sections 1332, 1334 that extend toward the distal end 1108 of the cartridge jaw 1102. The sections 1332, 1334 surround a gap 1336 that is defined between the sections 1332, 1334. When the electronics system 1300 is coupled to the end effector 1100, the gap 1336 is positioned over the slot 1134 defined in the floor 1122 of the cartridge jaw 1102. Accordingly, when the I-beam 350 is positioned in the proximal cavity 1144 in its pre-firing position, the sections 1332, 1334 of the bottom board 1304 may surround the blade or other component of the I-beam 350.

Referring now to FIGS. 14-17, an embodiment of an end effector 1100 including an electronics system 1400 may be used with a surgical stapler 100 having a handpiece. The system 1400 includes a board support 1402, which may be formed from rigid plastic or another appropriate structural material. The board support 1402 includes a U-shaped frame 1404 that includes a bend 1406 and two arms 1408, 1410 extending distally from the bend 1406. A gap 1412 is defined between the two arms 1408, 1410.

The board support 1402 further includes a board holder 1414 extending upward from the arm 1408. The board holder 1414 includes a slot that receives a circuit board or other electronic component. Illustratively, the board holder 1414 receives a main board 1416 for the electronics subsystem 1400. The main board 1416 illustratively includes a processor or controller 1418 and one or more magnetic sensors 1420, such Hall effect sensors. The main board 1416 may include additional electronic components in other embodiments.

The board support 1402 also includes a magnet holder 1422 that extends upward from the arm 1410. The magnet holder 1422 includes a slot that receives a permanent magnet 1424. As shown, the permanent magnet 1424 is positioned opposite a portion of the main board 1416, which illustratively includes the magnetic sensor 1422.

The electronics system 1400 further includes a near-field communication (NFC) board 1426 coupled to the main board 1416. The NFC board 1426 includes an antenna 1428, which may be used for RFID or other near-field communication functions. The system 1400 also includes a flex lead 1430, which electrically connects the electronics system 1400 to additional electronics of the surgical stapler 100 (not shown).

Figure 15:
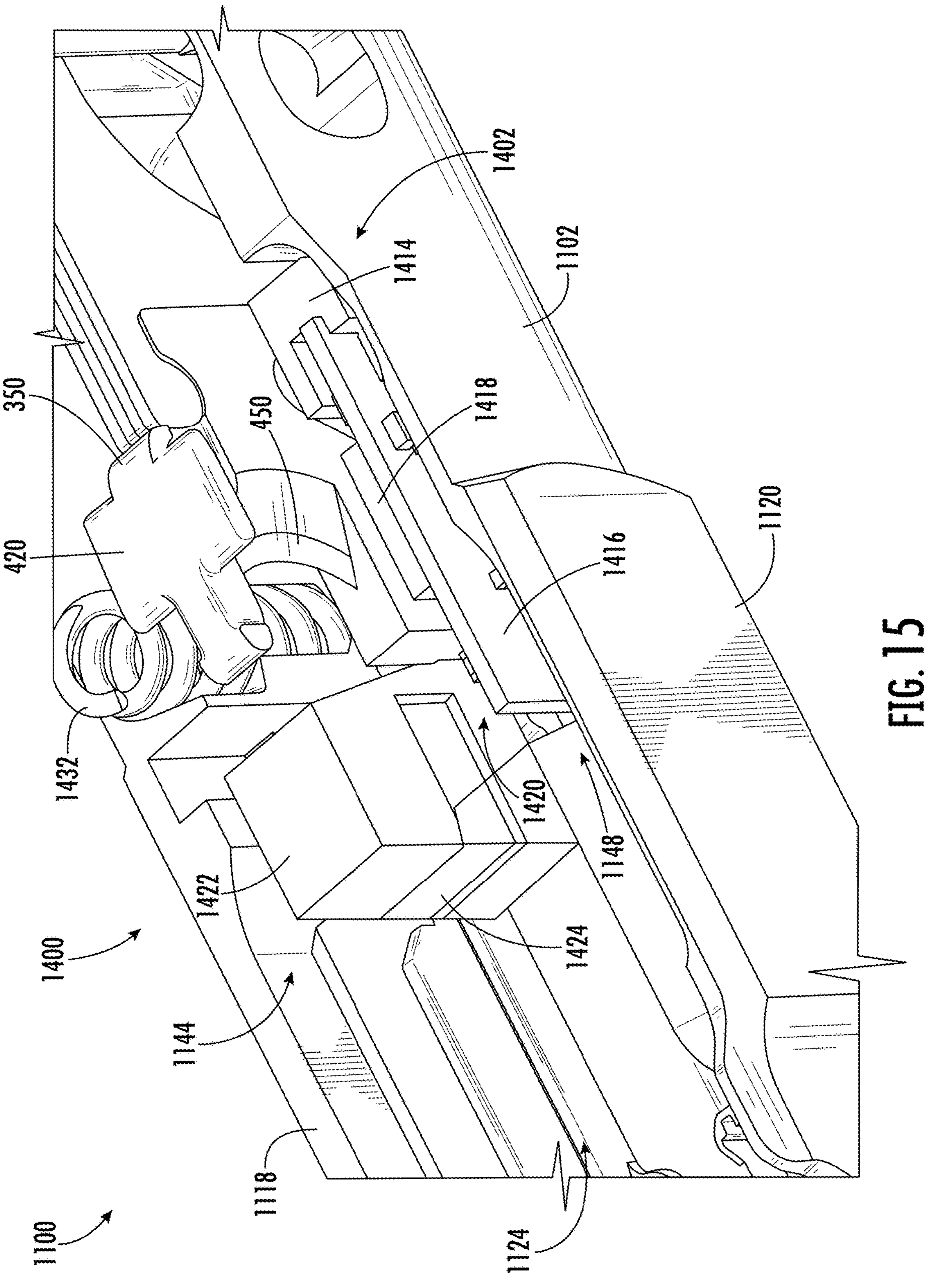
FIG. 15 is a perspective view of the electronics system of FIG. 14 installed in the end effector of FIGS. 11-12.
Figure 16:
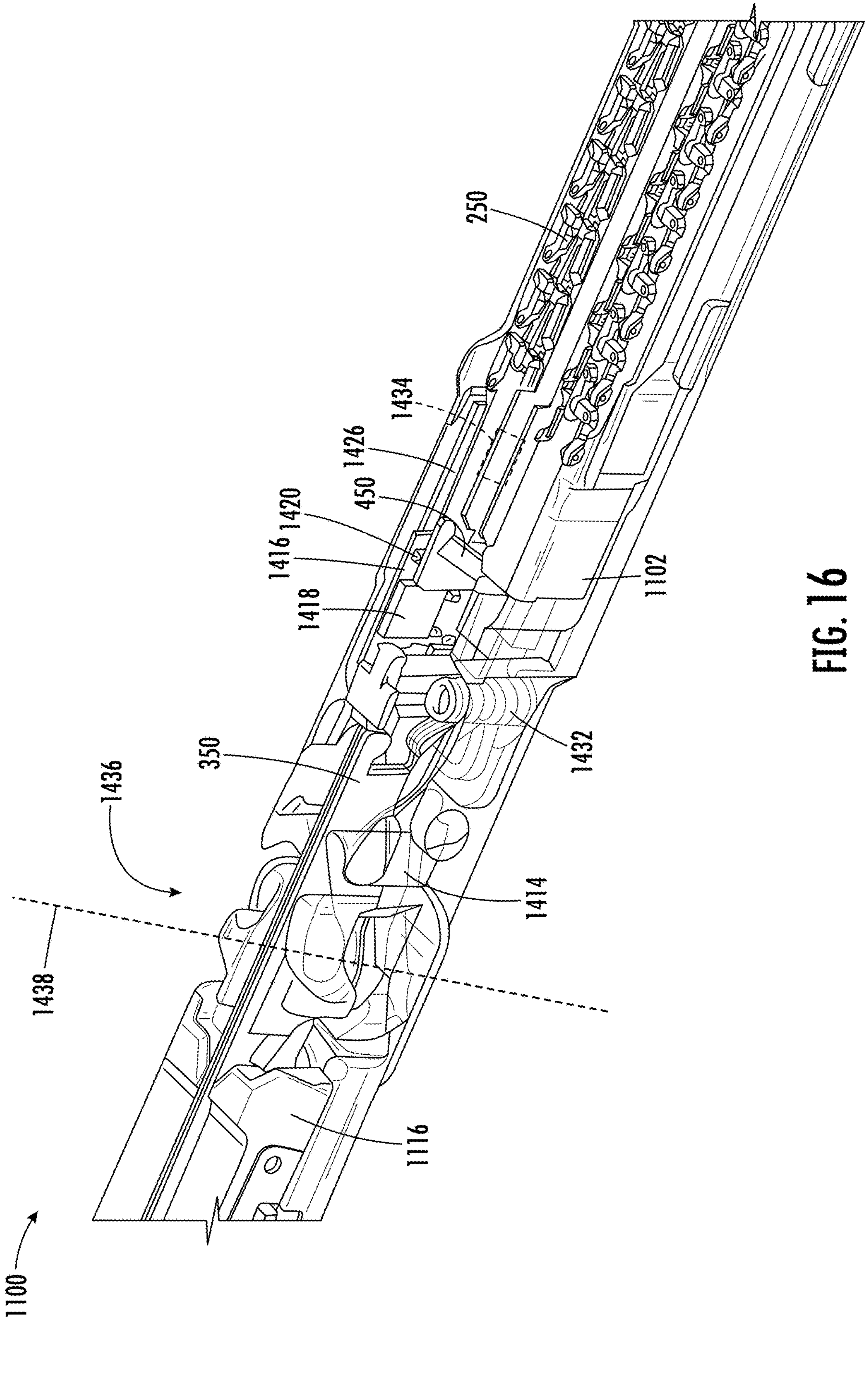
FIG. 16 is a cutaway view of the electronics system of FIG. 14 installed in the end effector of FIGS. 11-12.

As shown in FIGS. 15-16, electronics system 1400 may be coupled to the cartridge jaw 1102 of the end effector 1100. As shown, when the electronics system 1400 is coupled to the end effector 1100, the board support 1402 is positioned in the proximal cavity 1144 of the cartridge jaw 1102. The main board 1416 is positioned adjacent to the side wall 1120 of the cartridge jaw 1102. The permanent magnet 1424 is positioned on the opposite side of the cavity 1144. The NFC board 1426 extends distally from the main board 1408 toward the channel 1124, and is also positioned adjacent to the side wall 1120.

When the I-beam 350 is positioned in the proximal cavity 1144 in its pre-firing position, the board support 1402 surrounds the I-beam 350. As shown, the bend 1406 is positioned proximally of the knife 450, and the arms 1408, 1410 extend distally on either side of the knife 450. The arms 1408, 1410 fit above the lower beam 410 and below the upper beam 420. Accordingly, the knife 450 fits within the gap 1412 defined between the arms 1408, 1410.

The end effector 1100 further includes a spring bias lifter 1432, which is illustratively a helical spring, and is positioned within the proximal cavity 1144 between the side wall 1418 and the board support 1402, proximal of the permanent magnet 1424. In use, the spring bias lifter 1432 biases the anvil jaw 1110 toward the open position. During the firing operation, the I-beam 350 urges the anvil jaw 1110 to move toward the closed position, overcoming the force of the spring bias lifter 1432.

As shown in FIG. 16, a staple reload cartridge may be attached to the cartridge jaw 1102 within the channel 1124. The illustrative cartridge includes a radio frequency identification (RFID) tag 1434. When the cartridge is coupled to the cartridge jaw 1102 as shown in FIG. 16, the RFID tag 1434 is positioned adjacent to the antenna 1428 on the NFC board 1426. Accordingly, the electronics system 1400 may use the NFC board 1426 to sense the presence of the RFID tag 1434, which indicates that a cartridge has been attached to the cartridge jaw 1102 and/or may provide identifying information or other data related to the loaded cartridge.

Figure 17:
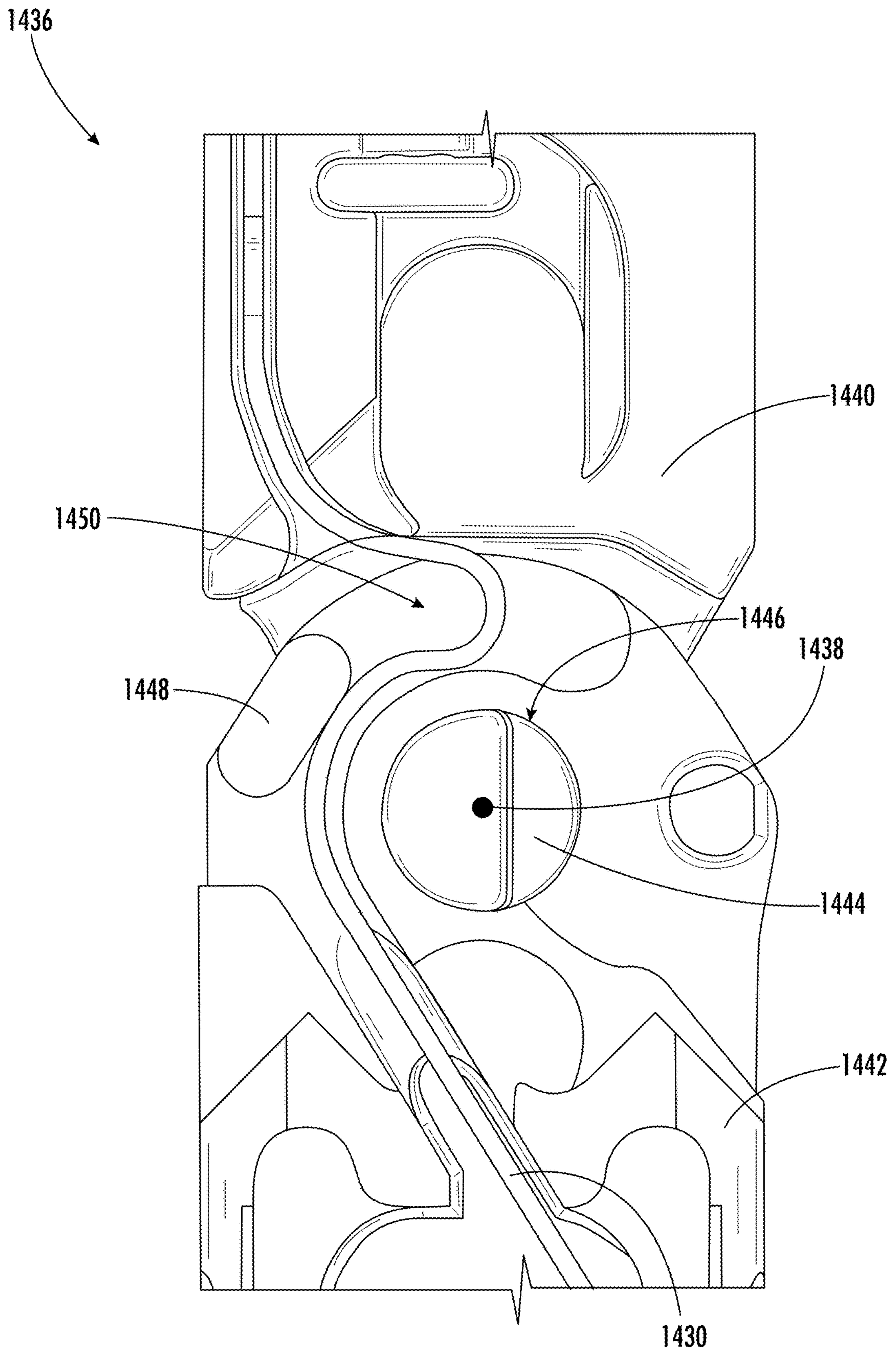
FIG. 17 is a top view of the electronics system of FIG. 14 installed in the end effector of FIGS. 11-12.

As shown in FIGS. 16-17, the flex lead 1430 extends proximally from the main board 1408 through the shaft of the surgical stapler 100. The shaft illustrative includes a joint 1436 which allows rotation of the end effector 1100 about an imaginary axis 1438 that extends transverse from the shaft. Such rotation may be referred to as yaw rotation. As best shown in FIG. 17, the joint 1436 illustratively includes two parts 1440, 1442 which are rotatably coupled with a post 1444 extending from the part 1440 and a hole 1446 defined in the part 1442 which receives the post 1444. Additionally or alternatively, although illustrated as two parts 1440, 1442 of the shaft 1416, it should be understood that the joint 1436 may be positioned at a different location, for example including a distal of the shaft and a corresponding proximal end of the end effector.

As shown, the flex lead 1430 extends proximally through the joint 1436. A boss 1448 extends upward from the part 1442. A slack bend 1450 is formed in the flex lead 1430. As the part 1442 is rotated relative to the part 1440, the slack bend 1450 increases curvature and straightens accordingly, and the boss 1448 retains the flex lead 1430 within the lateral dimensions of the shaft.

Figure 18:
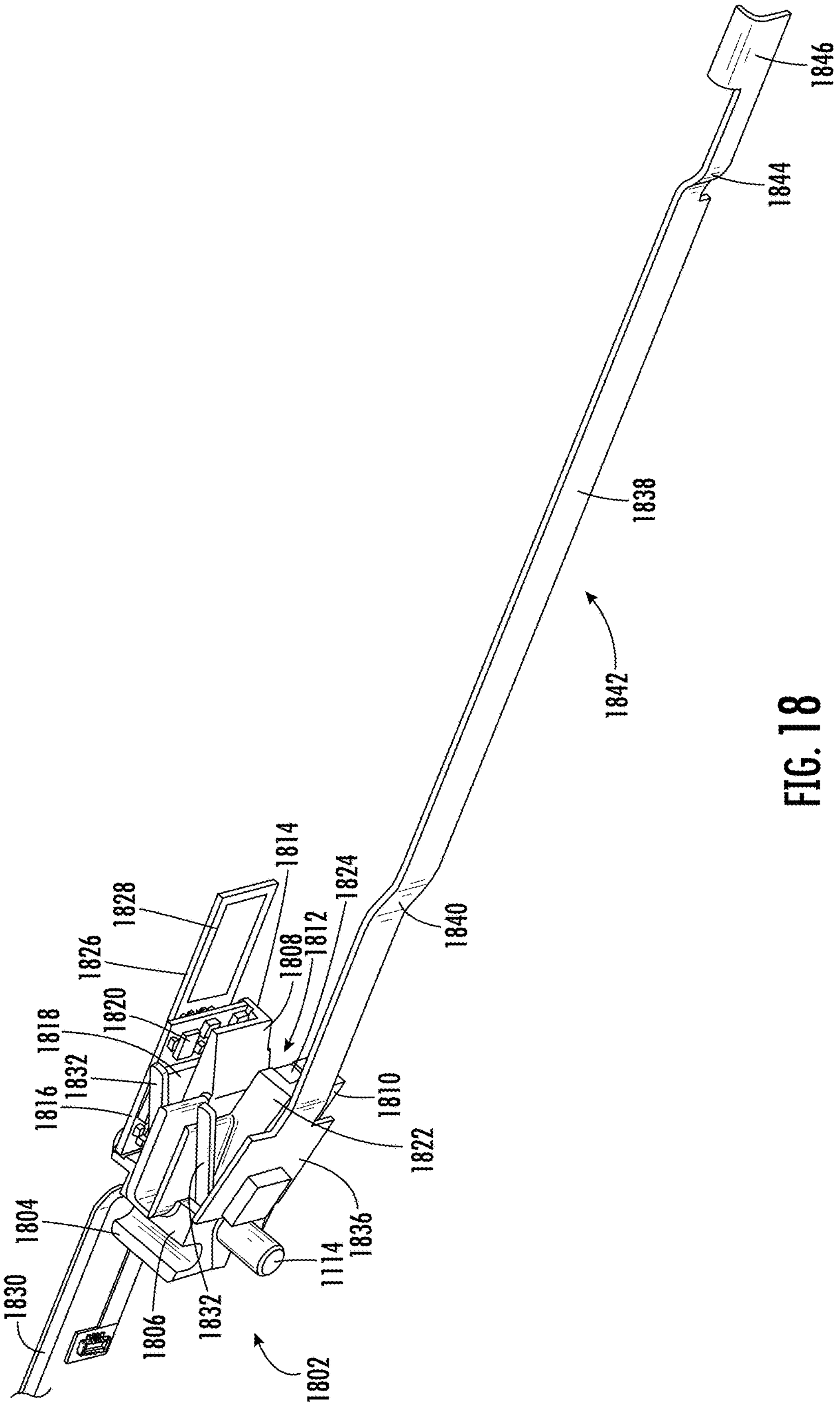
FIG. 18 is a perspective view of another embodiment of an electronics system that may be included in an end effector of FIGS. 11-12.
Figure 19:
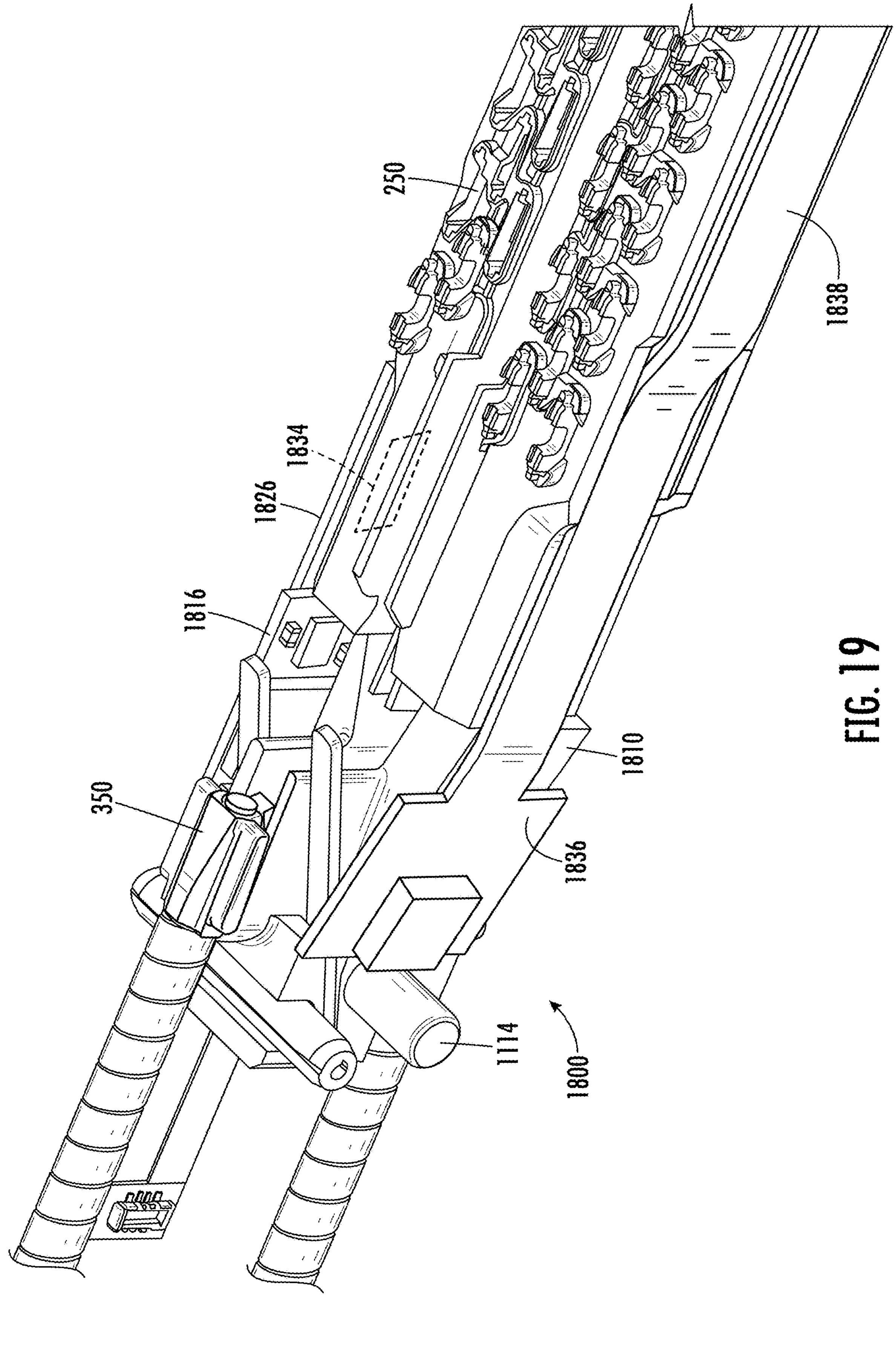
FIG. 19 is a perspective view of the electronics system of FIG. 18 with a staple cartridge reload that may be used with the end effector of FIGS. 11-12.
Figure 20:
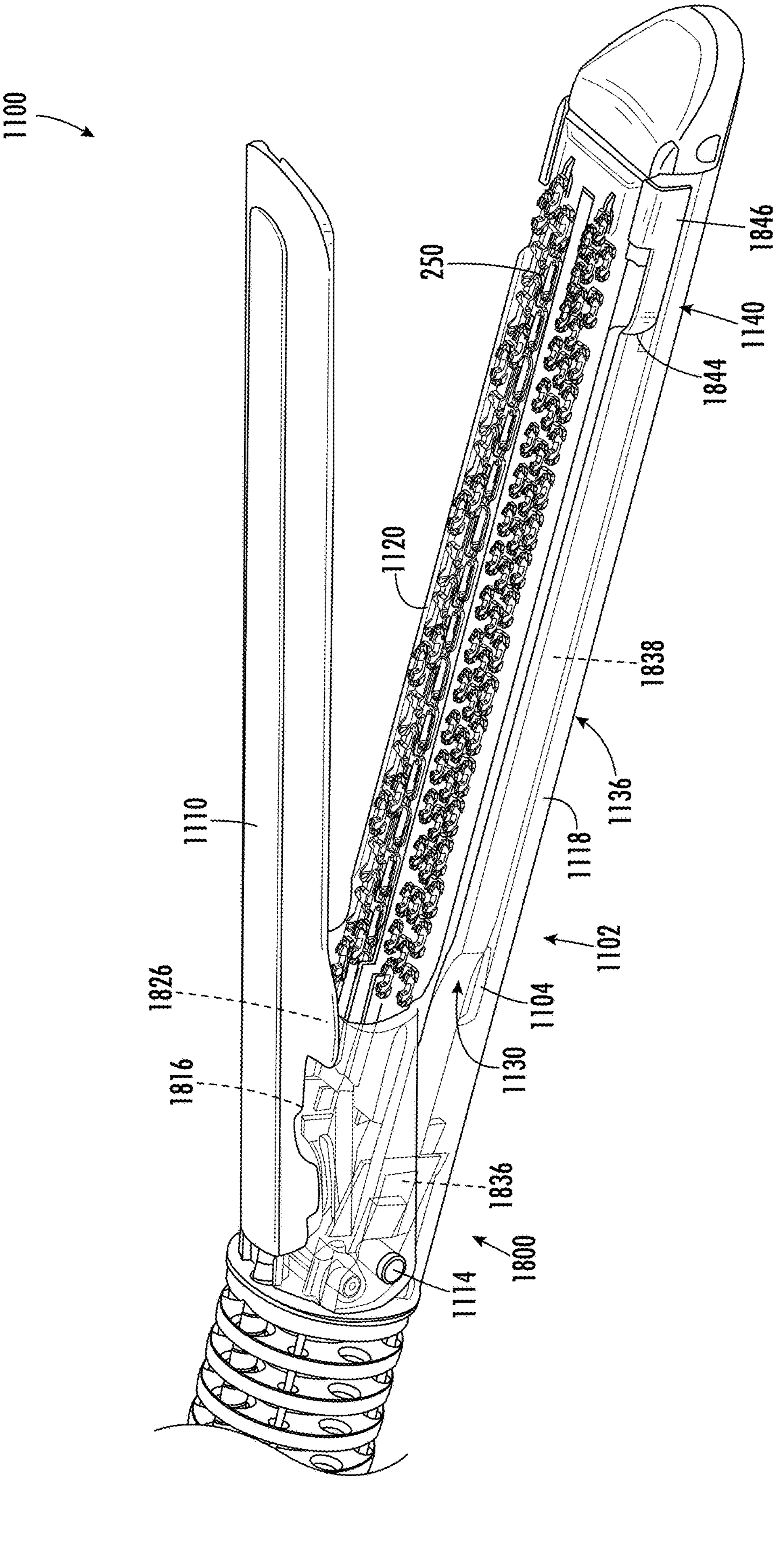
FIG. 20 is a cutaway view of the electronics system of FIG. 18 installed in the end effector of FIGS. 11-12.

Referring now to FIGS. 18-20, an embodiment of an end effector 1100 including an electronics system 1800 may be used with a surgical stapler 100 having a robotic tool interface. The system 1800 includes a board support 1802, which may be formed from rigid plastic or another appropriate structural material. The board support 1802 includes a frame 1804 that includes a proximal part 1806 and two arms 1808, 1810 extending distally from the proximal part 1806. A gap 1812 is defined between the two arms 1808, 1810.

The board support 1802 further includes a board holder 1814 extending outward from the arm 1808. The board holder 1814 includes a slot or other mechanism that receives a circuit board or other electronic component. Illustratively, the board holder 1814 receives a main board 1816 for the electronics subsystem 1800. The main board 1816 illustratively includes a processor or controller 1818 and a magnetic sensor 1820, such as a Hall effect sensor. The main board 1816 may include additional electronic components in other embodiments.

The board support 1802 also includes a magnet holder 1822 that is integrated in the arm 1810. The magnet holder 1822 includes a slot that receives a permanent magnet 1824. As shown, the permanent magnet 1824 is positioned opposite a portion of the main board 1816, which illustratively includes the magnetic sensor 1822.

The electronics system 1800 further includes a near-field communication (NFC) board 1826 coupled to the main board 1816. The NFC board 1826 includes an antenna 1828, which may be used for RFID or other near-field communication functions. The system 1800 also includes a flex lead 1830, which electrically connects the electronics system 1800 to additional electronics of the surgical stapler 100 (not shown).

As shown in FIGS. 19-20, the electronics system 1800 may be coupled to the cartridge jaw 1102 of the end effector 1100. As shown, when the electronics system 1800 is coupled to the end effector 1100, the board support 1802 is positioned in the proximal cavity 1144 of the cartridge jaw 1102. The main board 1816 is positioned adjacent to the side wall 1120 of the cartridge jaw 1102. The permanent magnet 1824 is positioned on the opposite side of the cavity 1144. The NFC board 1826 extends distally from the main board 1808 toward the channel 1124, and is also positioned adjacent to the side wall 1120.

When the I-beam 350 is positioned in the proximal cavity 1144 in its pre-firing position, the board support 1802 surrounds the I-beam 350. As shown, the proximal part 1806 is positioned proximally of the knife 450, and the arms 1808, 1810 extend distally on either side of the knife 450. The arms 1808, 1810 fit above the lower beam 410 and below the upper beam 420. Accordingly, the knife 450 fits within the gap 1812 defined between the arms 1808, 1810.

The end effector 1100 further includes a pair of spring bias lifters 1832, which are illustratively leaf springs, and are positioned within the proximal cavity 1144 extending over each of the arms 1808, 1810. In use, the spring bias lifters 1832 bias the anvil jaw 1110 toward the open position. During the firing operation, the I-beam 350 urges the anvil jaw 1110 to move toward the closed position, overcoming the force of the spring bias lifters 1832.

As shown in FIGS. 19-20, a staple reload cartridge may be attached to the cartridge jaw 1102 within the channel 1124. The illustrative cartridge includes a radio frequency identification (RFID) tag 1834. When the cartridge is coupled to the cartridge jaw 1102 as shown in FIG. 16, the RFID tag 1834 is positioned adjacent to the antenna 1828 on the NFC board 1826. Accordingly, the electronics system 1800 may use the NFC board 1826 to sense the presence of the RFID tag 1834, which indicates that a cartridge has been attached to the cartridge jaw 1102 and/or may provide identifying information or other data related to the loaded cartridge.

As shown in FIGS. 18-20, the electronics system 1800 further includes a tissue sensing board 1836 attached to the arm 1810 of the board support 1802. The tissue sensing board 1836 may be electrically coupled to the main board 1416, for example by one or more flex connectors positioned below the proximal part 1806 of the board support 1802 or other connection. The system 1800 further includes a distal sensing board 1838 that is electrically coupled to the tissue sensing board 1836 by one or more flex connectors 1840 and/or other circuit boards, cables, wires, or other connectors. Additionally, as shown in FIGS. 18-20, the system 1800 may further include an external board extension 1846, which is coupled to the tissue distal sensing board 1838 by another flex connector 1844.

When installed in the end effector 1100 as shown in FIGS. 19-20, the distal sensing board 1838 is positioned within the groove 1130 defined in the inner surface 1126 of the side wall 1118 of the cartridge jaw 1102. Accordingly, the distal sensing board 1838 may be positioned adjacent to the reload cartridge and otherwise close to the distal end 1108 of the end effector 1100. Further, the flex connector 1844 passes through the notch 1140, and the external board extension 1846 is attached to the outer surface 1136 of the side wall 1118. The tissue sensing board 1836, the distal sensing board 1838, and/or the external board extension 1846 includes one or more tissue sensors 1842, which are configured to sense one or more parameters of tissue located near the end effector 1100. For example, the tissue sensors 1842 may be embodied as capacitance sensors, impedance sensors, temperature sensors, or other sensors configured to determine environmental properties at the end effector 1100. In some embodiments, sensors 1842 that operate with direct contact to tissue may be positioned on the external board extension 1846. Additionally or alternatively, in some embodiments, the tissue sensing board 1836, the distal sensing board 1838, and/or the external board extension 1846 may include additional or different electronics and/or sensors, including magnetic sensors or other electronic devices.

Figure 21:
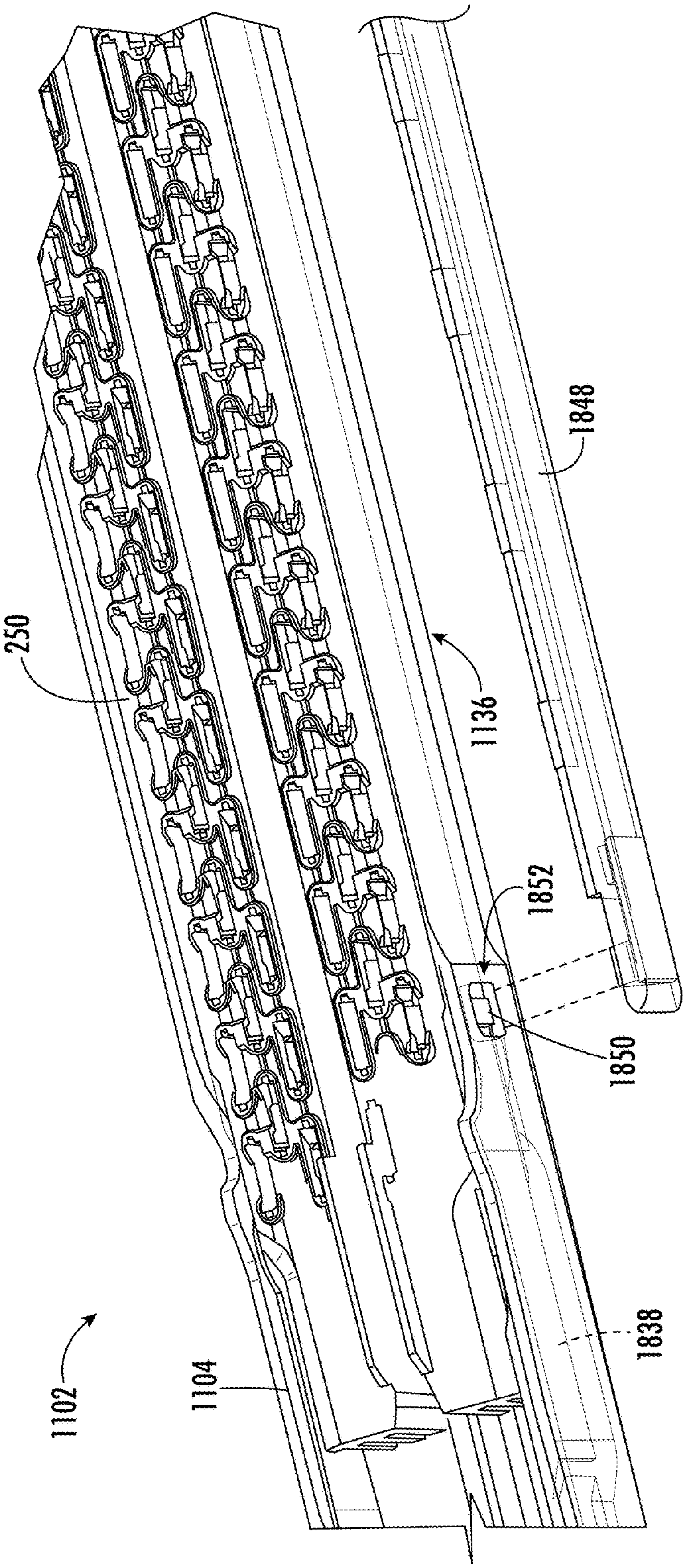
FIG. 21 is a cutaway view of another potential embodiment of the electronics system of FIG. 18 installed in the end effector of FIGS. 11-12.

Referring now to FIG. 21, another potential embodiment of the electronics system 1800 is shown with the system 1800 installed in the end effector 1100 and a reload cartridge positioned in the cartridge jaw 1102 of the end effector. In the system 1800 shown in FIG. 21, the system 1800 includes an external distal sensing board 1848, which may be attached to the outer surface 1136 of the side wall 1118 of the cartridge jaw 1102. When attached, the external distal sensing board 1848 is electrically coupled to the tissue sensing board 1836 and/or the distal sensing board 1838 via a pass-through connector 1850, which passes through an opening 1852 defined in the side wall 1118. According, in the illustrative embodiment shown in FIG. 21, the external distal sensing board 1848 may directly contact tissue of the patient surrounding the end effector 1100.

Although illustrated as including a certain arrangement of sensing boards, it should be understood that in other embodiments the end effector may include a different arrangement and/or other configuration of circuit boards, sensing boards, and/or other electronic components. For example, in an embodiment, the end effector may include two distal sensing boards positioned in the respective grooves 1130, 1132 surrounding the channel 1124. Additionally or alternatively, in an embodiment the end effector may include two external distal sensing boards positioned on both respective outer surfaces 1136, 1138. Additionally or alternatively, in an embodiment the end effector may include one distal sensing board positioned in a groove, and another external distal sensing board positioned on an external surface. Continuing that example, in such embodiments the cartridge jaw 1102 may be asymmetric, for example including a single internal groove 1130 defined in the side wall 1118 and an opening 1852 and external shelf or other attachment point defined in the other side wall 1120.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

EXAMPLES

Example 1 includes a surgical instrument comprising an end effector comprising an elongated jaw that extends from a proximal end to a distal end, wherein the jaw comprises a first side wall, a second side wall, and a floor coupled between the first side wall and the second side wall, wherein the first side wall, the second side wall, and the floor cooperate to define a first cavity positioned at the proximal end and a channel extending from the first cavity to the distal end; an I-beam having a knife and being moveable from a first position within the first cavity to a second position at the distal end of the channel; and a first circuit board coupled to the elongated jaw within the first cavity, wherein the first circuit board is adjacent to the I-beam when the I-beam is in the first position.

Example 2 includes the subject matter of Example 1, and wherein the first circuit board is coupled to the first side wall.

Example 3 includes the subject matter of Example 2, and further comprising: a second circuit board coupled to the floor of the elongated jaw within the first cavity; and a first flex connector that electrically couples the first circuit board and the second circuit board.

Example 4 includes the subject matter of Example 3, and wherein: the floor of the elongated jaw defines an elongated slot that extends from the first cavity to the distal end; and the second circuit board comprises a first section and a second section that cooperate to define a gap between the first section and the second section, wherein the gap is aligned with the elongated slot.

Example 5 includes the subject matter of any of Examples 3 and 4, and further comprising: a third circuit board coupled to the second side wall within the first cavity; and a second flex connector that electrically couples the second circuit board and the third circuit board.

Example 6 includes the subject matter of any of Examples 1-5, and wherein: the first side wall comprises an inner wall surface that faces the channel, wherein the first side wall defines a first inner groove that is in communication with the channel; and the surgical instrument further comprises (i) a second circuit board coupled to the first side wall within the first inner groove and (ii) a first flex connector that electrically couples the first circuit board and the second circuit board.

Example 7 includes the subject matter of any of Examples 1-6, and wherein: the first side wall comprises an outer wall surface, wherein the outer wall surface defines a first outer groove; a first opening is defined in the first side wall, wherein the first opening is in communication with the channel; and the surgical instrument further comprises a second circuit board coupled to the first side wall within the first outer groove, wherein the second circuit board is electrically coupled to the first circuit board via the first opening.

Example 8 includes the subject matter of any of Examples 1-7, and wherein the first circuit board comprises a processing circuit or a sensing circuit.

Example 9 includes the subject matter of any of Examples 1-8, and further comprising a board support coupled to the elongated jaw and positioned within the first cavity, wherein: the board support comprises a first arm and a second arm coupled by a bend, wherein the first arm and the second arm define an opening toward the distal end of the elongated jaw, and wherein the first arm and the second arm surround the I-beam when the I-beam is in the first position; and wherein the first arm supports the first circuit board, wherein the first circuit board is adjacent to and aligned with the first side wall.

Example 10 includes the subject matter of Example 9, and further comprising a permanent magnet coupled to the second arm of the board support, wherein the permanent magnet is positioned opposite the first circuit board across the opening defined between the first arm and the second arm.

Example 11 includes the subject matter of Example 10, and further comprising a magnetic sensor coupled to the first circuit board and positioned opposite the permanent magnet.

Example 12 includes the subject matter of any of Examples 9 and 10, and further comprising a near-field communication antenna board electrically coupled to the first circuit board and extending toward the distal end of the elongated jaw, wherein the near-field communication antenna board is adjacent to and aligned with the first side wall.

Example 13 includes the subject matter of any of Examples 9-12, and further comprising:

an elongated shaft that extends from a distal end to a proximal end, wherein the distal end is coupled to the end effector, and wherein the elongated shaft comprises a drivetrain coupled to the I-beam; and a flexible connector electrically coupled to the first circuit board and extending through the elongated shaft.

Example 14 includes the subject matter of Example 13, and further comprising a handpiece coupled to the proximal end of the elongated shaft, wherein the handpiece is electrically coupled to the flexible connector and is configured to drive the drivetrain; or a robotic tool interface coupled to the proximal end of the elongated shaft, wherein the robotic tool interface is electrically coupled to the flexible connector and is configured to drive the drivetrain.

Example 15 includes the subject matter of any of Examples 13 and 14, and wherein the elongated shaft comprises a joint, the flexible connector comprises a slack bend positioned at the joint, and the joint comprises a boss extending from the shaft that retains the flexible connector within a boundary of the elongated shaft.

Example 16 includes the subject matter of any of Examples 9-15, and further comprising an elongated anvil extending from a proximal end to a distal end, wherein the proximal end is hingedly coupled to a hinge positioned at the proximal end of the elongated jaw, wherein the anvil is rotatable about the hinge from an open position in which the distal end of the anvil is spaced apart from the distal end of the jaw to a closed position in which the distal end of the anvil is close to the distal end of the jaw.

Example 17 includes the subject matter of Example 16, and further comprising a leaf spring positioned in the first cavity and configured to bias the anvil to the open position, wherein the leaf spring is positioned between the board support and the anvil.

The invention claimed is:

1. A surgical instrument comprising:

an end effector comprising an elongated jaw that extends from a proximal end to a distal end, wherein the jaw comprises a first side wall, a second side wall, and a floor coupled between the first side wall and the second side wall, wherein the first side wall, the second side wall, and the floor cooperate to define a first cavity positioned at the proximal end and a channel extending from the first cavity to the distal end;

an I-beam having a knife and being moveable from a first position within the first cavity to a second position at the distal end of the channel; and a first circuit board coupled to the elongated jaw within the first cavity, wherein the first circuit board is adjacent to the I-beam when the I-beam is in the first position; wherein:

the first side wall comprises an outer wall surface, wherein the outer wall surface defines a first outer groove;

a first opening is defined in the first side wall, wherein the first opening is in communication with the channel; and the surgical instrument further comprises a second circuit board coupled to the first side wall within the first outer groove, wherein the second circuit board is electrically coupled to the first circuit board via the first opening.

2. The surgical instrument of claim 1, wherein the first circuit board is coupled to the first side wall.

3. The surgical instrument of claim 2, further comprising:

a third circuit board coupled to the floor of the elongated jaw within the first cavity; and a first flex connector that electrically couples the first circuit board and the third circuit board.

4. The surgical instrument of claim 3, wherein:

the floor of the elongated jaw defines an elongated slot that extends from the first cavity to the distal end; and the third circuit board comprises a first section and a second section that cooperate to define a gap between the first section and the second section, wherein the gap is aligned with the elongated slot.

5. The surgical instrument of claim 3, further comprising:

a fourth circuit board coupled to the second side wall within the first cavity; and a second flex connector that electrically couples the third circuit board and the fourth circuit board.

6. The surgical instrument of claim 1, wherein:

the first side wall comprises an inner wall surface that faces the channel, wherein the first side wall defines a first inner groove that is in communication with the channel; and the surgical instrument further comprises (i) a third circuit board coupled to the first side wall within the first inner groove and (ii) a first flex connector that electrically couples the first circuit board and the third circuit board.

7. The surgical instrument of claim 1, wherein the first circuit board comprises a processing circuit or a sensing circuit.

* * * * *